US010434200B2

(12) United States Patent
Reb et al.

(10) Patent No.: US 10,434,200 B2
(45) Date of Patent: *Oct. 8, 2019

(54) COMPOSITIONS AND ASSOCIATED METHODS FOR RADIOISOTOPE-BINDING MICROPARTICLES

(71) Applicant: Biosphere Medical, Inc., South Jordan, UT (US)

(72) Inventors: Philippe Reb, Themericourt (FR); Celine Chaix, Paris (FR)

(73) Assignee: Biosphere Medical, Inc., South Jordan, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 15/615,586

(22) Filed: Jun. 6, 2017

(65) Prior Publication Data
US 2017/0333579 A1  Nov. 23, 2017

Related U.S. Application Data

(63) Continuation of application No. 14/207,219, filed on Mar. 12, 2014, now Pat. No. 9,687,573.

(60) Provisional application No. 61/779,712, filed on Mar. 13, 2013.

(51) Int. Cl.
*A61K 51/12* (2006.01)
*A61K 9/00* (2006.01)

(52) U.S. Cl.
CPC ..... *A61K 51/1244* (2013.01); *Y10T 428/2982* (2015.01)

(58) Field of Classification Search
CPC ............................. A61K 51/00; A61K 51/1251
See application file for complete search history.

(56) References Cited

U.S. PATENT DOCUMENTS

| | | |
|---|---|---|
| 3,334,050 A | 8/1967 | Grotenhuis et al. |
| 4,123,396 A | 10/1978 | Rembaum et al. |
| 4,224,177 A | 9/1980 | Macedo et al. |
| 4,224,427 A | 9/1980 | Mueller et al. |
| 4,789,501 A | 12/1988 | Day et al. |
| 4,889,707 A | 12/1989 | Day et al. |
| 4,981,625 A * | 1/1991 | Rhim ............... A61K 9/1635 264/10 |
| 4,994,013 A | 2/1991 | Suthanthiran et al. |
| 5,011,677 A | 4/1991 | Day et al. |
| 5,011,797 A | 4/1991 | Day et al. |
| 5,030,195 A | 7/1991 | Nardi |
| 5,039,326 A | 8/1991 | Day et al. |
| 5,069,816 A | 12/1991 | Desantis et al. |
| 5,162,267 A | 11/1992 | Smyth |
| 5,163,896 A | 11/1992 | Suthanthiran et al. |
| 5,182,051 A | 1/1993 | Bandy et al. |
| 5,302,369 A | 4/1994 | Day et al. |
| 5,342,283 A | 8/1994 | Good |
| 5,424,288 A | 6/1995 | Order |
| 5,496,545 A | 3/1996 | Holmes-Farley et al. |
| 5,614,652 A | 3/1997 | Filler et al. |
| 5,667,775 A | 9/1997 | Holmes-Farley et al. |
| 5,762,903 A | 6/1998 | Park et al. |
| 5,792,475 A | 8/1998 | Davis et al. |
| 5,863,284 A | 1/1999 | Klein |
| 5,885,547 A | 3/1999 | Gray |
| 5,888,546 A | 3/1999 | Ji et al. |
| 5,894,022 A | 4/1999 | Ji et al. |
| 5,942,209 A | 8/1999 | Leavitt et al. |
| 6,015,541 A | 1/2000 | Greff et al. |
| 6,039,970 A | 3/2000 | Callegaro et al. |
| 6,060,040 A * | 5/2000 | Tournier ............... A61K 49/06 424/9.364 |
| 6,083,495 A | 7/2000 | Holmes-Farley et al. |
| 6,099,457 A | 8/2000 | Good |
| 6,103,295 A | 8/2000 | Chan et al. |
| 6,168,777 B1 | 1/2001 | Greff et al. |
| 6,210,436 B1 | 4/2001 | Weadock |
| 6,214,315 B1 | 4/2001 | Greff et al. |
| 6,231,615 B1 | 5/2001 | Preissman |
| 6,241,962 B1 | 6/2001 | Nicolini et al. |
| 6,248,057 B1 | 6/2001 | Mavity et al. |
| 6,258,338 B1 | 7/2001 | Gray |

(Continued)

FOREIGN PATENT DOCUMENTS

| | | |
|---|---|---|
| CA | 2307190 A1 | 5/1999 |
| CA | 2307191 A1 | 5/1999 |

(Continued)

OTHER PUBLICATIONS

Scranton, et al., BioMedical Applications of Polyelectrolykes, Adv. Polymer. Sol. 122, ,1995 ,1-54.
Shaw, et al., Retention Characteristics of Lanthanide Ions on a Mixed Phosphonic Acid-Carboxylic Acid Cation Exchanger, Aust. J. Chem., 56, ,2003 ,201-206.
Stubbs, et al., Selective Internal Radiation Therapy (SIRT) with 90Yttrium Microspheres for Extensive Coloractal Liver Metastases, Hepato-Gastroenterology, 48, ,2001 ,333-337.
Stubbs, et al., Selective Internal Radiation Therapy with 90Yttrium Microspheres for Extensive Colorectal Liver Metastases, J. Gastrointest. Surg. 5(3), ,2001 ,294-302.
Van Es, et al., Tumour Embolization of the Vx2 Rabbit Head and Neck Cancer Model with Dextran Hydrogel and Holmium-Poly (L-Lactic Acid) Microspheres: A Radionuclide and Histological Pilot Study, Journal of Cranio-Maxillogacial Surgery, 29, ,2001 ,28.

(Continued)

Primary Examiner — Michael G. Hartley
Assistant Examiner — Jagadishwar R Samala
(74) Attorney, Agent, or Firm — Stoel Rives LLP

(57) ABSTRACT

The present disclosure relates to polymeric materials that may be labeled with a radioisotope, to processes for producing the labeled polymeric material, and to methods of using the materials in analytical and therapeutic applications. Specifically, the disclosure relates to injectable and implantable microparticles, such as microspheres, which are associated with radioisotopes such that the microparticles are both therapeutic and detectable. The radioisotope-containing microparticles are useful for embolization and other therapeutic medical applications.

16 Claims, 11 Drawing Sheets

(56) References Cited

U.S. PATENT DOCUMENTS

| | | | |
|---|---|---|---|
| 6,273,851 B1 | 8/2001 | Slater et al. | |
| 6,296,831 B1 | 10/2001 | Weller et al. | |
| 6,328,700 B1 | 12/2001 | Rheinhardt et al. | |
| 6,333,020 B1 | 12/2001 | Wallace et al. | |
| 6,335,028 B1 | 1/2002 | Vogel et al. | |
| 6,348,184 B1 | 2/2002 | Nicolini et al. | |
| 6,352,682 B2 | 3/2002 | Leavitt et al. | |
| 6,355,275 B1 | 3/2002 | Klein | |
| 6,368,586 B1 | 4/2002 | Jacob et al. | |
| 6,379,648 B1 | 4/2002 | Day et al. | |
| 6,436,424 B1 | 8/2002 | Vogel et al. | |
| 6,589,502 B1 | 7/2003 | Coniglione et al. | |
| 6,660,301 B1 | 12/2003 | Vogel et al. | |
| 6,746,661 B2 | 6/2004 | Kaplan | |
| 6,818,199 B1 | 11/2004 | Hainfeld et al. | |
| 2002/0068089 A1 | 6/2002 | Vogel et al. | |
| 2002/0114763 A1 | 8/2002 | Glajch et al. | |
| 2002/0187172 A1* | 12/2002 | Reb | A61K 49/18 424/401 |
| 2002/0197326 A1 | 12/2002 | Vogel et al. | |
| 2003/0118658 A1 | 6/2003 | Trogolo et al. | |
| 2003/0120355 A1* | 6/2003 | Hafeli | A61K 51/1251 700/1 |
| 2003/0215519 A1 | 11/2003 | Schwarz et al. | |
| 2004/0091425 A1 | 5/2004 | Boschetti | |
| 2004/0258614 A1 | 12/2004 | Line et al. | |
| 2006/0067883 A1 | 3/2006 | Krom et al. | |

FOREIGN PATENT DOCUMENTS

| | | | |
|---|---|---|---|
| CA | 2369983 A1 | 11/2000 | |
| CA | 2370124 A1 | 11/2000 | |
| CA | 2393539 A1 | 6/2001 | |
| EP | 1371365 B1 | 9/2005 | |
| WO | 2000066183 A8 | 1/2001 | |
| WO | 2002034300 A1 | 5/2002 | |
| WO | 2003004930 A1 | 1/2003 | |
| WO | 2004040972 A3 | 10/2004 | |
| WO | 2005035005 A1 | 4/2005 | |
| WO | 2006036269 | 4/2006 | |
| WO | 2008034911 | 3/2008 | |
| WO | 2005061009 A3 | 5/2008 | |

OTHER PUBLICATIONS

Volkert, et al., Therapeutic Radiopharaceuticals, Chemical Reviews, vol. 99, No. 9, ,1999 ,2269-2292.
Zielinski, et al., Synthesis and Quality Control Testing of 32P Labeled Ion Exchange Resin Microspheres for Radiation Therapy of Hepatic Neoplasms, Int. J. Appl. Radial. Isot. vol. 34, No. 9, , 1983 ,1343-1350.
European Search Report dated Jun. 11, 2009 for EP04809310.
Extended European Search Report dated May 31, 2013 for EP121939334.
Extended European Search Report dated Sep. 23, 2016 for EP14776008.6.
International Search Report and Written Opinion dated Jun. 27, 2014 for PCT/US2014/025023.
International Search Report dated Jan. 28, 2008 for PCT/US2004/007061 (WO2005/035005).
International Search Report dated May 16, 2007 for PCT/US2005/025645.
Notice of Allowance dated Apr. 26, 2017 for U.S. Appl. No. 14/207,219.
Office Action dated Feb. 7, 2007 for U.S. Appl. No. 10/407,144.
Office Action dated Feb. 24, 2006 for U.S. Appl. No. 10/407,144.
Office Action dated Mar. 20, 2013 for U.S. Appl. No. 11/185,449.
Office Action dated Apr. 9, 2010 for U.S. Appl. No. 11/185,449.
Office Action dated Apr. 18, 2014 for U.S. Appl. No. 13/462,004.
Office Action dated Apr. 22, 2014 for U.S. Appl. No. 11/185,449.
Office Action dated Apr. 28, 2016 for U.S. Appl. No. 14/207,219.
Office Action dated Jul. 14, 2006 for U.S. Appl. No. 10/407,144.
Office Action dated Jul. 27, 2007 for U.S. Appl. No. 10/688,768.
Office Action dated Aug. 9, 2011 for U.S. Appl. No. 11/185,449.
Office Action dated Aug. 11, 2009 for U.S. Appl. No. 11/185,449.
Office Action dated Sep. 8, 2008 for U.S. Appl. No. 10/688,768.
Office Action dated Sep. 10, 2015 for U.S. Appl. No. 14/207,219.
Office Action dated Sep. 27, 2010 for U.S. Appl. No. 11/185,449.
Office Action dated Oct. 21, 2016 for U.S. Appl. No. 14/207,219.
Office Action dated Nov. 12, 2008 for U.S. Appl. No. 11/185,449.
Office Action dated Dec. 19, 2006 for U.S. Appl. No. 10/688,768.
Andrews, et al., Hepatic Radioembolization with Yttrium-90 Containing Glass Microspheres: Preliminary Results and Clinical Follow-Up, The Journal of Nuclear Medicine, vol. 35 No. 10, ,1994 , 1637-1644.
Ariel, et al., Therapeutic Intralymphatic Infusion of Radioactive Isotopes, Journal of Nuclear Medicine, Society of Nuclear Medicine, ,Jan. 1, 1963 ,186.
Business Wire, et al., Biosphere Medical Launches Nes EmboGold Microspheres ,Sep. 6, 2001.
Campbell, et al., Analysis of the Distribution of Intra-Arterial Microspheres in Human Liver Following Hepatic Yttrium-90 Microsphere Therapy, Phys. Med. Biol. 45, ,2000 ,1023-1033.
Campbell, et al., Tumour Dosimetry in Human Liver Following Hepatic Yttrium-90 Microsphere Therapy, Phys. Med Biol. 46, , 2001 ,487-498.
Demar, et al., Comparison of Gas Clearance and Radioactive Microspheres for Pancreatic Blood Flow Measurement, Pancreas, vol. 4, No. 2, ,1989 ,161-168.
Ehrhardt, et al., Therapeutic use of 90Y Microspheres, Nucl. Med. Biol., vol. 14, No. 3, ,1987 ,233-242.
Ercan, et al., Radioactive Microparticles, Part I: Preparation, MML Series, vol. 2, ,1999 ,283-307.
Ercan, et al., Radioactive Microparticles, Part II: Medical Applications, MML Series, vol. 2, ,1999 ,313-342.
Feinendgen, et al., Editorial—Microdosimetric Considerations of Hapatic Radloembolization, The Journal of Nuclear Medicine, vol. 35 No. 10, ,1994 ,1644-1646.
Gray, et al., Randomised Trial of SIR-Spheres® Plus Chemotherapy vs. Chemotherapy Alone for Treating Patients with Liver Metastases from Primary Large Bowel Cancer, Annals of Oncology, vol. 12, ,2001 ,1711-1720.
Hafeli, et al., Hepatic Tumor Radioembolization in a Rat Model Using Radioactive Themium (186RE/188RE) Glass Microspheres, Int. J. Radiation Oncology Biol. Phys. vol. 44, No. 1, ,1999 , 189-199.
Ho, et al., Clinical Evaluation of the Partition Model for Estimating Radiation Doses from Yttrium-90 Microspheres in the Treatment of Hepatic Cancer, European Journal of Nuclear Medicine, vol. 24 No. 3, ,1997 ,293-298.
Ho, et al., Intrahepatic 90 Y-Microspheres for Hepatocellular Carcinoma, The Journal of Nuclear Medicine 42(10), ,2001 ,1587-1588.
Laurent et al., Trisacryl Gelatin Microspheres for Therapeutic Embolization, I: Development and In Vitro Evaluation, American Journal of Neuroradiology, vol. 17 ,1996 ,533-540.
Lin, et al., Effects of 90Y-Microspheres on Liver Tumors: Comparison of Intratumoral Injection Method and Intra-Arterial Injection Method, The Journal of Nuclear Medicine 41(11), ,2000 , 1892-1987.
Loehman, et al., Preparation and Propertis of Yttrium-Silicon-Aluminum Oxynitride Glasses, The Journal of the American Ceramic Society 62(9-10), ,1979 ,491-494.
Maus, et al., Microparticles Based on Biocompatible, Biodegradable Polymers. Possible Surrogates for Y-90?, Journal of Nuclear Medicine, vol. 52 ,May 1, 2011 ,1594.
Mumper, et al., Neutron-Activated Holmium-166-Poly (L-Lactic Lactic Acid) Microspheres: A Potential Agent for the Internal Radiation Therapy of Hepatic Tumors, Journal of Neclear Medicine, vol. 32 No. 11, ,1991 ,2139-2143.
Nijsen, et al., Advances in Nuclear Oncology: Microspheres for Internal Radionuclide Therapy of Liver Tumors, Current Medicinal Chemistry, 9, ,2002 ,73-82.

(56) References Cited

OTHER PUBLICATIONS

O'Leary, et al., Periodic Table Groups, 1-6. http://www.ucc.ei/academic/chem/dolchem/html/elem/group.html, ,2000.
Park, et al., Radioisotope Carrying Polyethylene Oxide-Polycaprolactone Copolymer Micelles for Tagetable Bone Imaging, Biomaterials 23, ,2002 ,873.
Raymond, et al., Production of Radioactive particles for Endovascular Therapeutic Interventions, Biomaterials, 27, ,2006 ,1566-1572.
Rudershausen, et al., Novel Chelator containing Particles Specific for Controlled Radiosotope Delilvery, Journal of Labeled Compounds and Radiopharmaceuticals, vol. 44, No. S1 ,May 1, 2001.
Schafer, et al., Chromatographic Characterization of a Phosphate-Modified Zirconia Support for Bio-Chromatographic Applications, Journal of Chromatography, 587 ,1991 ,149-160.
Schafer, et al., Physical and Chemical Characterization of a Porous Phosphate-Modified Zirconia Substrate, Journal of Chromatography, 587(2), ,Dec. 20, 1991 ,137-147.

\* cited by examiner

COMPOSITIONS AND ASSOCIATED METHODS FOR RADIOISOTOPE-BINDING MICROPARTICLES

CROSS-REFERENCE TO RELATED APPLICATIONS

This application is a continuation of U.S. patent application Ser. No. 14/207,219, filed on Mar. 12, 2014, titled COMPOSITIONS AND ASSOCIATED METHODS FOR RADIOISOTOPE-BINDING MICROPARTICLES, which claims the benefit of U.S. Provisional Application No. 61/779,712, filed on Mar. 13, 2013, titled COMPOSITIONS AND ASSOCIATED METHODS FOR RADIOISOTOPE-BINDING MICROPARTICLES, the disclosure of each of which is incorporated herein by reference in its entirety.

TECHNICAL FIELD

The present disclosure relates generally to compositions of microparticles containing radioisotopes, methods for their delivery, methods for their therapeutic use, and kits thereof. In certain aspects, the present disclosure relates to compositions and methods for delivery of polymeric microspheres containing radioisotopes for the treatment of certain cancers.

DETAILED DESCRIPTION

Figure 1:
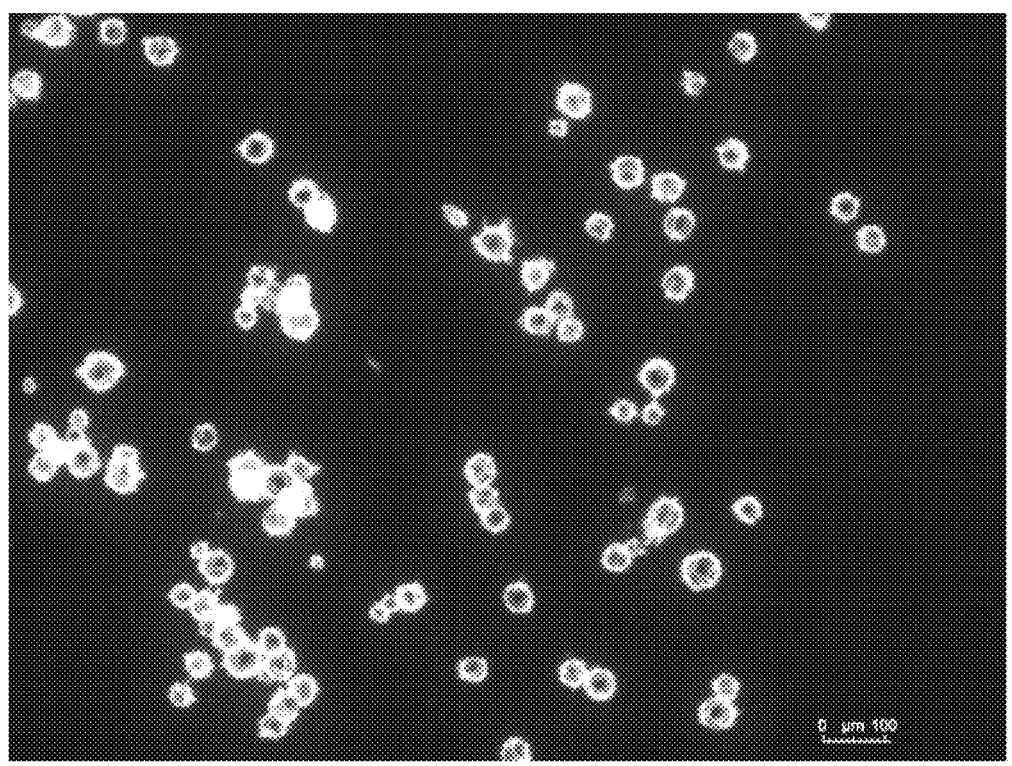
FIG. 1 is a microscope image of microparticles of Example 4 after lyophilization and prior to coupling to a chelating agent.

The present disclosure provides compositions of microparticles containing radioisotopes, methods for their delivery, methods for their therapeutic use, and kits thereof.

Therapeutic vascular embolization procedures are used to treat or prevent certain pathological situations in vivo. Generally, they are carried out using catheters or syringes under imaging control to position solid or liquid embolic agents in a target blood vessel.

Embolization can be used to occlude, partially or completely, vessels of a variety of organs including the brain, liver, and spinal cord, which results in reduced blood flow or complete occlusion of the vessels. One application of embolization is to stop or reduce blood flow in hemorrhagic situations. Another application is to stop delivery of blood supply and nutrients to tissue, for instance, to reduce or deny blood supply to a solid tumor. In the case of vascular malformations, embolization may enable the blood flow to the normal tissue, aid in surgery and limit the risks of hemorrhage. Depending on the pathological condition, embolization can be used for temporary as well as permanent therapeutic objectives.

Embolization has been performed with a variety of materials, such as small pieces of durable goods, including glass, polyvinyl alcohol particles, gelatin particles, liquid embolic products and spherical solid hydrogels. Commercially available embolic materials may be difficult to see or to trace in vivo because they are relatively transparent, cannot be seen clearly with normal light before and during administration, or are difficult to detect after administration because they are not radiopaque and lack features that render them detectable using magnetic resonance imaging, ultrasound, or nuclear medicine procedures.

The labeling of biocompatible polymeric materials, including emboli for vascular occlusion, is useful to properly detect, control, and/or study the effect of the implanted or injected material. Chemical dyes, magnetic resonance agents, and contrasting/radiopaque agents have all been used to serve such purposes. Radiopaque labeling of polymeric materials, which constitute the vast majority of implanted materials, has received the most attention. To improve the radio-visibility of the polymers, heavy elements may be incorporated into the polymers to increase the average electron density and specific gravity. A radiopaque polymeric material, however, is only visible by x-rays, which may not be appropriate for use in specific medical situations. An additional method for labeling biocompatible polymeric materials would be beneficial.

One potential method is via isotopic labeling, including labeling with radioactive isotopes. Biocompatible polymeric material labeled with a radioisotope may be useful therapeutically, such as to treat tumors, as well as for analytical or diagnostic purposes.

Attachment of certain radioactive isotopes to polymeric microparticles, however, is challenging. A balance must be found between the activity of the isotope used for the label, and the type of polymeric material chosen, as the radioactivity may affect the physical stability of the polymer. In some instances, use of an isotope which degrades the polymeric material may be advantageous, such as, for example, with biodegradable polymeric materials. In other instances, use of more durable polymeric material is favored. The manner (i.e., covalent or ionic) and timing (i.e. immediately prior to injection/implantation or during polymerization of the microparticle) of the association of the radioisotope with the microparticle should be considered, as well, and will also likely be use-dependent.

In addition, the development of microparticles, including microspheres, for radionuclide therapy is complicated by the difficulty in determining the in vivo biodistribution of the microspheres. The biodistribution of microparticles is significant for radiotherapy because the microparticle should be in close physical proximity to the tumor or physiological area being treated. It would be useful to associate a material with the microparticle that is capable of emitting a detectable, non-hazardous signal, which would allow for the determination of the radiation dose distribution in the tissue. Thus, any tumor tissue that escaped effective radiotherapy ("cold spots") could be detected, and would indicate retreatment. An example of such a signal is a γphoton (gamma-photon) of appropriate energy. Radioisotopes that emit γphotons suitable for diagnostic imaging include technetium-99m, indium-111, gallium-67, iodine-131, holmium-166, rhenium-188, rhenium-186, lanthanum-140, samarium-153, dysprosium-166, erbium-169, ytterbium-175, lutetium-177 and thallium-201. Similarly, $^{18}F$ (as its anion) may be used, although $^{18}F$ does not emit gamma-photons directly; it emits positrons, which react with surrounding electrons to generate gamma-photons.

Most clinical radiopharmaceuticals are diagnostic agents incorporating a gamma-emitting radionuclide which, because of the physical or metabolic properties of its coordinated ligands, localizes in a specific organ after intravenous injection. The resultant images can reflect organ structure or function. These images are obtained by means of a gamma camera that detects the distribution of ionizing radiation emitted by the radioactive molecules.

Mammalian cancer is often identified using a gamma camera, which provides images of potential tumors in the body by detecting the radiation emitted by a radiopharmaceutical given to a patient undergoing a full-body scan. In such systemic approaches, suspected tumor regions collect higher concentrations of the radiopharmaceutical, which produces a higher count rate and, therefore, a detectable contrast between the tumor region and its surroundings.

A gamma camera has a collimator to focus the gamma photons emitted by the patient's body, a scintillator to convert the gamma photons into light photons or scintillations, and an array of photomultiplier tubes, each of which converts the scintillations into electrical pulses. Such a detection system is followed by a processing and display unit which may be used to obtain an image projection of the distribution of the radioactive isotopes in the patient during the acquisition of the image.

The use of biocompatible polymeric materials in radionuclide therapy suggests that radiolabeled microparticles, including microspheres, may offer a promising treatment option for patients suffering from a variety of types of cancer. This treatment option may be particularly desirable for cancers with an extremely poor prognosis and/or without other adequate therapies, such as primary and metastatic malignancies of the liver. Microparticle delivery via the hepatic artery promises to be particularly effective for both primary and metastatic liver cancer since these tumors are well-vascularized compared to normal liver tissue and receive the bulk of their blood supply from the hepatic artery. In addition, many kinds of radiolabeled particles and radionuclides have been tested for local treatment of a variety of tumors in organs, including the liver, lung, tongue, spleen and soft tissue of extremities. See, for example, Gonsalves et al., Expert Rev. Gastroenterol. Hepatol. 2(4), 453-456 (2008) and Liepe et al., Cancer Biotherapy and Radiopharmaceuticals, 15(3), 261-265 (2000).

The internal delivery of radioactivity, compared to external delivery by radioactive beams, allows for the use of less penetrating radioactive sources and, by definition, healthy tissues do not have to be traversed to reach the target. Hence embolization of the tumoral vascular bed with radioactive microparticles allows for delivery of a large radiation dose directly to the tumor, while minimizing radiation damage to surrounding tissues. In situ radiation can also palliate recanalization, a drawback associated with particle embolization. This type of treatment provides a highly selective application of suitable radioactive particles (such as, for example, highly energetic β-emitters) to deliver high doses of therapeutic radiation to the tumor, with as little surrounding tissue damage as possible.

Glass, resin, albumin, and polymeric microparticles associated with a material that emits β-particles upon neutron activation have been described. Polymer-based microparticles have many advantages over other materials, in particular their near-plasma density, biocompatibility, and if desirable, their ability to biodegrade. The neutron activation may be accomplished by subjecting the β-particle-associated material to a high flux of thermal neutrons, usually within or near the core of a reactor.

Patients with primary or metastatic tumors may be treated by radio-embolization via a catheter or direct injection of microparticles into the tumor with a needle. Previous studies describe the administration of microparticles to patients via a catheter, whereby the catheter tip was placed in the hepatic artery. The particles eventually lodge in the microvasculature of the liver and tumor, remaining until the complete decay of the radioisotope. The blood flow within the liver may also be temporarily redirected in favor of the tumor by a bolus infusion of a vasoconstrictor, and the particles may then be embolized into the arterial circulation. While external beam radiation causes radiation hepatitis at doses above 30-35 Gy, the liver can tolerate up to 80-150 Gy using such internal radionuclide therapy. Increased patient longevity, pain relief, tumor response and total clinical improvement are frequently reported after such treatment.

Commercial radioactive particles used for microparticle emboli may contain a radioactive β-emitting particle and a chemical dye, magnetic resonance agent, or contrasting agent. In general, however, these microparticles lack features that render them detectable using nuclear medicine procedures such as visualization by a gamma camera.

Therefore, there is a need for a method of labeling implantable or injectable polymeric materials in general, and small embolic materials in particular, such that the materials can be detected readily by radiologic imaging techniques. At the same time, the labeling should be biocompatible and physically stable at the implantation or injection site.

The present disclosure provides polymeric materials that are associated with radioisotopes, processes for producing the labeled polymeric materials, injectable solutions and kits comprising the materials, and methods of using the materials in prophylactic and therapeutic applications. The disclosure describes two approaches for association of the radioisotope to the polymeric material via chelation; one involving polymerization of the chelating moiety with the polymers used to form the material (i.e. as a monomer), and one involving addition of the chelating moiety to the polymeric material after the material has been initially polymerized. These approaches are discussed herein.

I. Definitions

Unless specifically defined otherwise, technical terms as used herein have their normal meaning as understood in the art. The following terms are specifically defined for the sake of clarity.

The articles "a" and "an" are used herein to refer to one or more than one (i.e. to at least one) of the grammatical object of the article. By way of example, "an element" means one element or more than one element.

As used herein, the term "metal" refers to elements which possess chemically metallic character, including the alkali metals, alkaline earth metals, transition metals, post-transition metals, metalloids, rare earth metals, lanthanides and actinides. A metal may be a radioisotope.

As used herein, the terms "chelate" or "chelating" refer to the physicochemical process describing the interaction between a ligand (or, the "chelating agent") and a metal cation (e.g., the isotope), wherein the metal cation is associated to the chelating agent by at least two bonds, defining a ring with the metal. The bonds may be formed through any type of physical or chemical interaction, including a covalent bond, ionic bond, or van der Waal's bond.

As used herein, the term "radionuclide" refers to a radioactive isotope (i.e. a radioisotope) or element.

Throughout the application, reference to a microparticle refers to a particle made of a polymer or combination of polymers formed into bodies of various sizes, including particles which may be irregularly shaped and which may be spherical in shape. A microparticle includes, for example, a microsphere or a microbead. A microparticle may include a radioisotope associated with or chelated to it, such as in a composite material.

As used herein, the term "microsphere" refers to a microparticle that is substantially spherical in shape and is equal to or less than about 2 mm in diameter. For example, the microparticle may be substantially spherical in shape and is equal to or less than about 1 mm in diameter.

"Substantially spherical," as used herein generally means a shape that is close to a perfect sphere, which is defined as a volume that presents the lowest external surface area. Specifically, "substantially spherical" as used herein means, when viewing any cross-section of the particle, the difference between the average major diameter and the average minor diameter is less than 20%, such as less than 10%. The surfaces of the microspheres disclosed herein may appear smooth under magnification of up to 1000 times. The microspheres may comprise, in addition to the particles, other materials as described and defined herein.

As used herein, the phrase "time of use" refers to the period during which a microsphere is implanted in a patient or subject.

As used herein, the phrase "associated with" means the condition in which two or more substances have any type of physical contact. For example, when a polymeric material is "associated with" metal or metal particles, the metal particles may be deposited on the surface of the polymeric material, within the material, or, if the material is porous, within the pores of the material, through any type of physical or chemical interaction such as through a covalent bond, ionic bond, or van der Waal's bond, or through impregnating, intercalating, or absorbing. The phrase "associated with" includes, for example, chelating. As used herein, when a polymeric material is associated with metal or metal particles (e.g., metal cations), it is "labeled" with the metal or metal compound particles.

As used herein, the term "implant" means a substance that is placed or embedded at least in part within the tissue of a mammal. An "implantable" substance is capable of being placed or embedded within the tissue through various means. For example, within the meaning herein, a traditional prosthetic device is an implant, as are substances such as microparticles, that are placed within or encompassed by the dermal tissue of a mammal.

As used herein, the terms "embolize" and "embolization" refer to the occlusion or blockage of a blood vessel. The occlusion or blockage may occur either due to blood clots or emboli as a result of a physiological condition or due to an artificial act of the embolic materials. In this regard, according to the present invention, an embolus is different from an implant.

As used herein, the terms "polymer" and "polymerize" refer to a molecule formed by the chemical association of two or more monomeric units. The monomeric units are normally associated by covalent linkages. The two or more monomeric units in a polymer can be all the same, in which case the polymer is referred to as a homopolymer. They can be also be different and, thus, the polymer will be a combination of the different monomeric units. These polymers are referred to as copolymers.

As used herein, the term "hydrogel" refers to a polymeric composition, comprising at least 50% water by weight, and can comprise a wide variety of polymeric compositions and pore structures.

The term "contrast-enhancing" refers to materials capable of being monitored during injection into a mammalian subject by methods for monitoring and detecting such materials, for example by radiography or fluoroscopy. Non-limiting examples of contrast-enhancing agents are radiopaque materials, paramagnetic materials, heavy atoms, transition metals, lanthanides, actinides, and dyes. Contrast-enhancing agents including radiopaque materials may be water soluble or water insoluble. Non-limiting examples of water soluble radiopaque materials include metrizamide, iopamidol, iothalamate sodium, iodomide sodium, and meglumine. Non-limiting examples of water insoluble radiopaque materials include metals and metal oxides such as iron, gold, titanium, silver, stainless steel, oxides thereof, aluminum oxide, and zirconium oxide.

As used herein, the term "injectable" means capable of being administered, delivered or carried into the body via a needle, a catheter, or other similar ways.

A "patient" refers to an animal in which radionuclide-labeled microspheres, as disclosed herein, will have a beneficial effect. In an embodiment, the patient is a human being.

II. Compositions

The compositions described herein are microparticles that may include at least one polymerized monomer, a chelating agent and a radioisotope which may be chelated by the chelating agent to associate the radioisotope to the polymerized monomer. Of course, if desired, the compositions described herein may include one or more additional constituents, such as a contrast-enhancing agent. Moreover, variations and combinations of components of the compositions described herein may be used, as appreciated by a skilled artisan with the aid of the present disclosure. For example, two or more crosslinking agents may be used. Alternatively, two or more compositions of microparticles may be used for the delivery of one or more radioisotopes. In one embodiment, the microparticle includes a copolymer of two polymerized monomers.

According to the present disclosure, the radioisotope-containing polymeric materials ("composite materials") may be used in a medical application, and they are suitable as implantable and/or injectable devices. In certain embodiments, the composite material is in microparticle form and is useful as emboli for prophylactic or therapeutic embolization. Therefore, the composite materials of the present disclosure are suitable in injectable implantation and embolization as small particles, such as microparticles or microspheres. These microparticles may be difficult to detect after injection into the body. In certain embodiments, the microparticles are rendered detectable by associating them with a suitable β-emitting and/or γ-emitting radioisotope.

Radionuclide therapeutic techniques using microparticles for the treatment of various ailments rely upon the precise and accurate delivery of microparticles to a target. This treatment option offers the promise of delivering therapy directly to the afflicted area while minimizing damage to nearby healthy tissue, a serious shortcoming associated with conventional treatment options such as chemotherapy, radiotherapy, or surgical resection. However, the effectiveness of treatments using radionuclide microparticles, including microspheres, can be improved by their formulation at the point of use (e.g., at a hospital's radiopharmacy). This allows physicians to prescribe customized doses of radiation to a patient. Therefore, a microparticle that could be associated with a radioactive isotope at the point of use is desirable. As disclosed herein, microparticles comprising a polymer and a chelating agent have been designed to associate with a radioisotope that emits a therapeutic β-particle. In certain embodiments, the radioisotope that emits a therapeutic β-particle also emits a diagnostic γ-ray.

In certain embodiments, the polymeric materials comprise microspheres based on biocompatible, hydrophilic, substantially spherical, non-biodegradable, and non-toxic polymers. The microspheres are injectable and/or implantable and may not be susceptible to digestion or elimination through the mammal's immune, lymphatic, renal, hepatic, pulmonary, or gastrointestinal system or otherwise. In some embodiments, the microspheres can be eliminated by the mammal.

As discussed above, embolization may be performed using angiographic techniques with guidance and monitoring, including fluoroscopic or X-ray guidance, to deliver an embolizing agent to vessels or arteries. Further, a vasodilator (e.g., adenosine) may be administered to the patient before, simultaneously, or subsequent to embolization, to facilitate the procedure.

While portions of the present disclosure include language relating to specific clinical applications of embolization, all types of embolization processes are considered to be within the contemplation of the described methods. Specifically, one of skill in the medical or embolizing art will understand and appreciate how microparticles as described herein can be used in various embolization processes by guiding a delivery mechanism to a desired vascular body site, and delivering an amount of the microspheres to the site, to cause restriction, occlusion, filling, or plugging of one or more desired vessels and reduction or stoppage of blood flow through the vessels. Factors that might be considered, controlled, or adjusted for, in applying the process to any particular embolization procedure may include the chosen composition of the microparticles (e.g., to account for imaging, tracking, and detection of a radiopaque particle substrate); the amount of microparticles delivered to the body site; the method of delivery, including the particular equipment (e.g., catheter) used and the method and route used to place the dispensing end of the equipment at the desired body site. Each of these factors will be appreciated by one of ordinary skill, and can be readily dealt with to apply the described methods to innumerable embolization processes.

With the aid of the present disclosure, it will be understood by those having skill in the art that a wide variety of monomers, chelating agents and radioisotopes may be incorporated into the microparticles disclosed herein. The disclosed monomers, chelating agents and radioisotopes are by way of example and not limitation.

(i) Monomers

A microparticle as disclosed herein can be fabricated from any hydrophilic polymer or copolymer. The polymeric material includes natural and synthetic polymers. For example, the natural polymer or derivative thereof may comprise gelatin, crosslinked gelatin, oxidized starch, alginate, gellan, gum arabic, galactan, arabinogalactan, chitosan, hyaluronan, chondroitin sulfate, keratan sulfate, heparan sulfate, dermatan sulfate, carboxymethylcellulose, oxidized cellulose, or related polymers. In certain embodiments, the material comprises one or more polymers selected from acrylates, acrylam ides, acrylics, vinyls, acetals, allyls, cellulosics, methacrylates, polyamides, polycarbonates, polyesters, polyim ides, polyolefins, polyphosphates, polyurethanes, silicones, styrenics, and/or polysaccharides.

In certain embodiments, one or more of the polymerized monomers is selected from at least one of the following: acrylate, acrylamide, methacrylate, methacrylamide, sodium acrylate, ethylene glycol methacrylate phosphate, N-[tris (hydroxymethyl)methyl]-acrylamide, vinylphosphonate, N, N-methylene-bis-acrylamide, N',N'-diallyl-tartardiamide, and glyoxal-bis-acrylamide. In certain embodiments, the polymeric material of the microparticle is or is made to be an elastomer, a hydrogel, a water-swellable polymer, or combinations thereof.

The polymer may be crosslinked. The crosslinker may be biodegradable or non-biodegradable. The crosslinker may be capable of resorption by a patient, or it may be non-resorbable.

In an embodiment, the polymeric material is a polymethacrylate, such as poly(methyl methacrylate) or poly(2-hydroxyethyl methacrylate).

In an embodiment, the polymeric material may comprise sodium acrylate. In an embodiment, the polymeric material may comprise a copolymer of N-[tris(hydroxymethyl) methyl]-acrylamide and sodium acrylate. The monomer may be a hydrophilic polymer or copolymer, and the polymeric material may comprise more than one monomer.

In certain embodiments, the microparticle comprises a polymeric material that comprises a hydrophilic copolymer, which contains, in copolymerized form, about 1% to about 99%, by weight, of sodium acrylate, and about 99% to about 1%, by weight, of N-[tris(hydroxymethyl)methyl]-acrylamide.

In an embodiment, the polymeric material is in microparticle form with dimensions ranging from between about 1 µm to about 2000 µm. In some embodiments, the microparticles are substantially spherical microspheres with diameters ranging from between about 10 µm to about 200 µm. In certain embodiments, the diameters range from between about 25 µm to about 35 µm. In other embodiments, the diameter is no more than about 25 µm, or no less than about 35 µm. In an embodiment, the diameter is about 30 µm.

The microparticle of the present disclosure is suitable for therapeutic vascular embolization purposes.

(ii) Chelating Agents

A microparticle as disclosed herein can include a chelating agent. In one embodiment, the chelating agent chelates a radioisotope and associates it with the polymerized monomer. In one embodiment, the chelating agent may be short enough to remain soluble in water yet long enough to chelate the appropriate radioisotope. For example, the chelating agent may contain a backbone chain of 4-18 non-hydrogen atoms, including carbon, oxygen, sulfur, and nitrogen atoms. The chelating agent may be partially or fully cyclic or heterocyclic, such as including cyclic ether, pyridine or imidazole rings. The types of chelating agents vary, and they may be present in their conjugate base form at around physiological pH.

In certain embodiments, the microparticles comprise a chelating agent to associate with a radioisotope. The chelating agent may be linked to the microparticle after polymerization of the microparticle, or it may be incorporated into the microparticle during polymerization as a monomer. In certain embodiments, the chelating agent may be introduced into the polymer in a separate step (e.g., by a grafting reaction).

Exemplary chelating agents which may be linked to the microparticle include mercaptoacetyltriglycine (MAG-3), and EDTA and derivatives thereof, including EGTA, BAPTA, DOTA, DTPA-monoamide, DOTA-R, DO3A-R, NOTA-Bn-R, NODASA-R, and NODAGA-R. These exemplary chelating agents are discussed in more detail below.

Mercaptoacetyltriglycine can chelate Re and further couple with a peptide, as shown below:

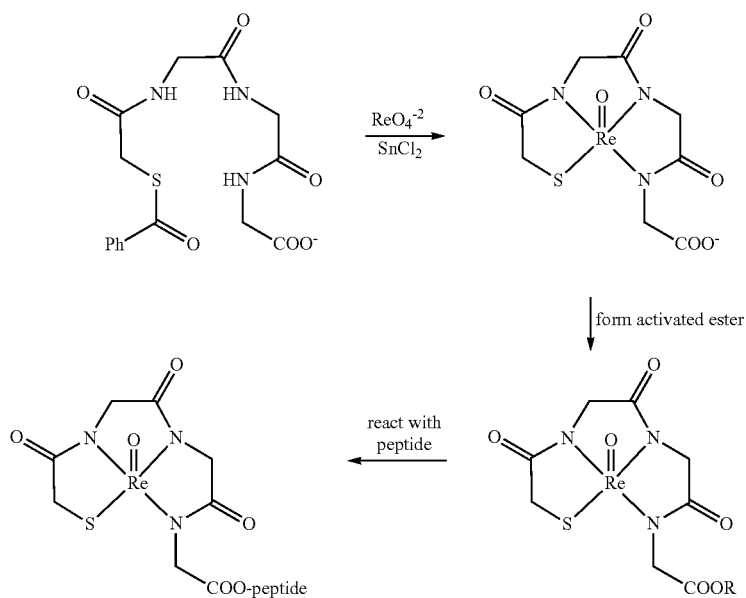

In a similar manner, replacement of the peptide group via the ester bond shown above, with a polymerizable group such as a methacrylate, allows for the use of a mercaptoacetyltriglycine chelating group to be associated with the microsphere:

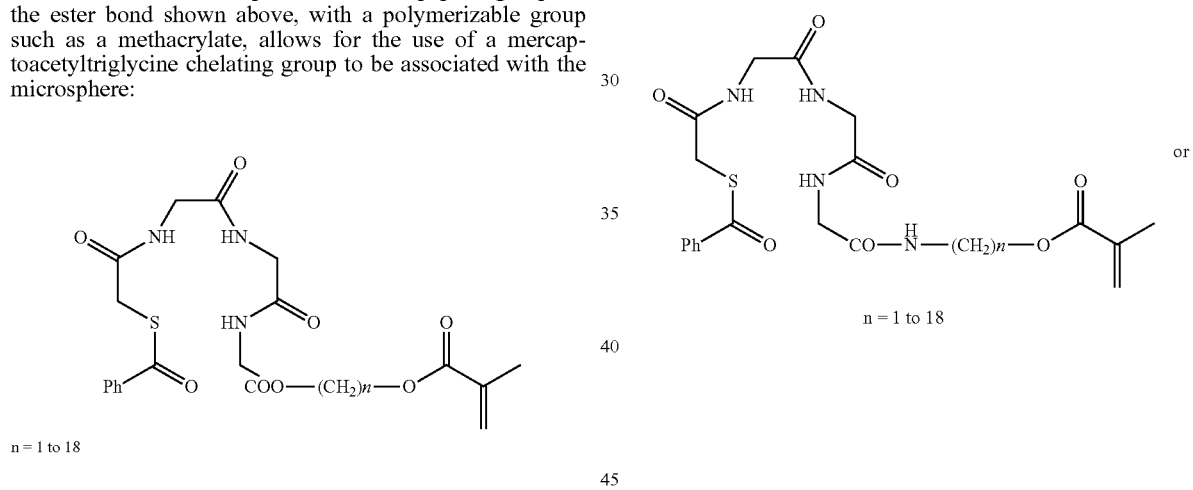

The use of such a monomer during the polymerization of the microparticle would allow the mercaptoacetyltriglycine to be incorporated into the polymer of the microparticle.

Alternatively, the polymerizable group may be linked directly to the mercaptoacetyltriglycine group via esterification, without an intervening $CH_2$ group:

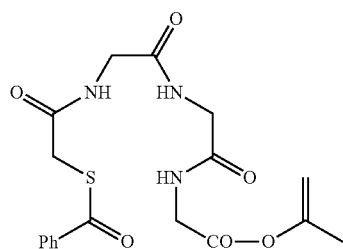 [SMILES: C=C(C)OC(=O)CNC(=O)CNC(=O)CNC(=O)CSC(=O)c1ccccc1]

Similarly, a polymerizable group may be linked directly to the mercaptoacetyltriglycine group via amidation, either with or without intervening $CH_2$ groups:

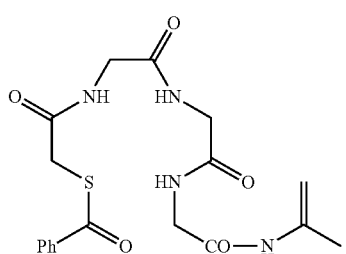

In an embodiment, the polymerizable group is an acrylate derivative, such as methacrylamide. For example, both an amide-linked and an ester-linked mercaptoacetyltriglycine chelating group may be used with methacrylamide to link the MAG-3 chelating group to a polymerizable group, either with or without intervening $CH_2$ groups:

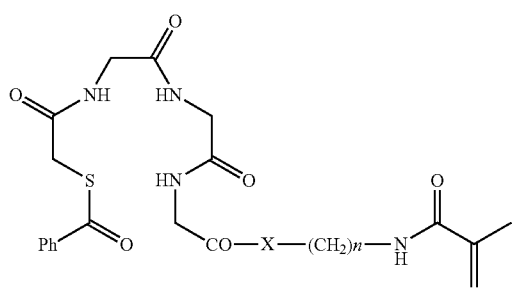

n = 1 to 18

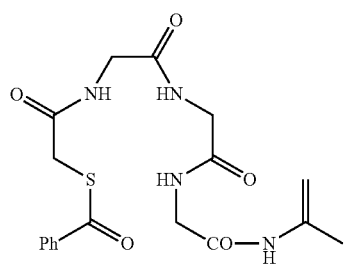

For example, the following MAG-3 derivatives may be used as chelating agents:

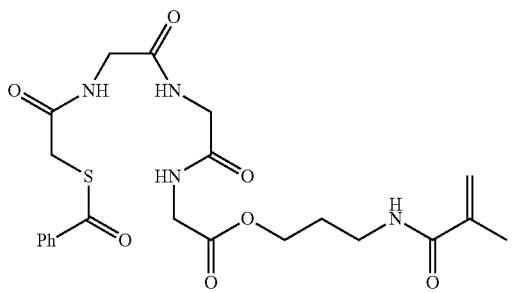

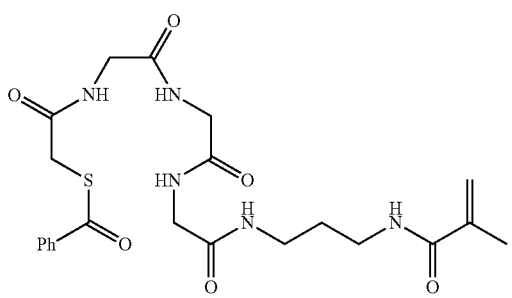

In an embodiment, the chelating agent is the MAG-3 derivative shown in Formula I:

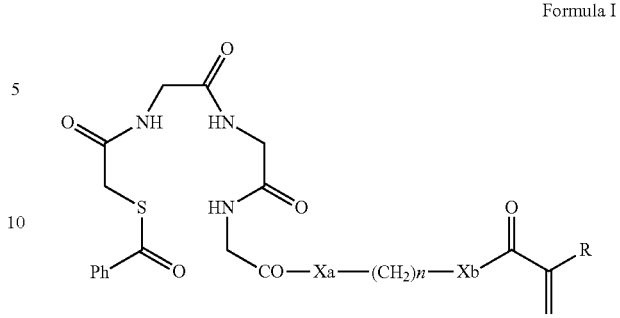

Formula I which contains a polymerizable group, wherein n may be between 1 and 18, inclusive; Xa and Xb may independently be O, S or N; and R may be alkyl or H. In certain embodiments, n is 3, Xa and Xb are O, and R is methyl. In other embodiments, n is 1. In further embodiments, n is between 1 and 10, inclusive; or is between 1 and 4, inclusive. The chelating agent may be incorporated into the microparticle during the polymerization of the particle as, for example, a monomer.

In some embodiments, the chelating agent is a MAG-3 derivative which is bound to the microparticle after the microparticle has been formed, via functionality present in the microparticle. For example, the microparticle may contain carboxylate functionality, which may react with an amine group of a MAG-3 derivative:

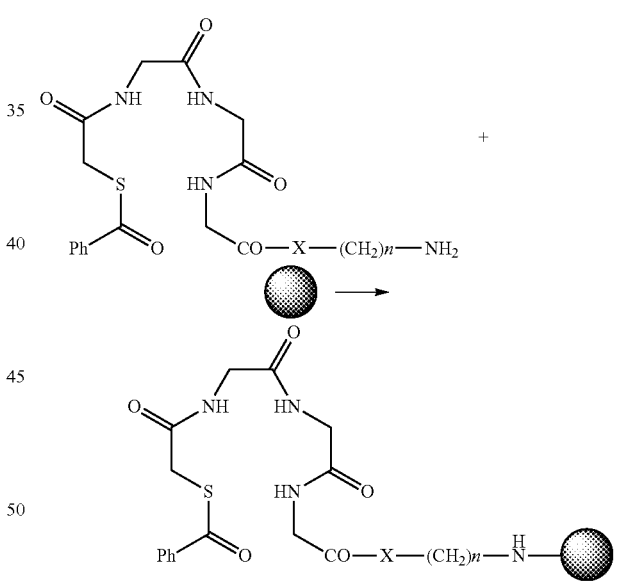

EDTA and its derivatives can complex numerous metals, including rhenium (Re). The structure of EDTA, or ethylenediaminetetraacetic acid, is:

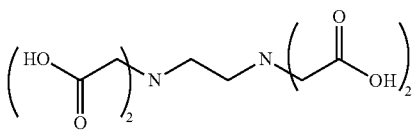

EDTA

Attachment of a polymerizable group to EDTA, such as a methacrylate, via for example an ester or amide bond, would allow for the use of a EDTA chelating group to be associated with the microsphere:

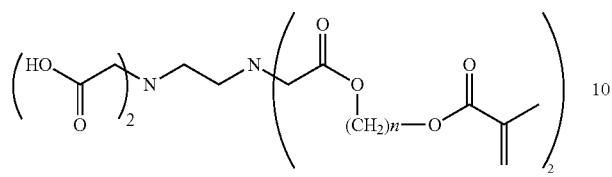

n = 1 to 18

The use of such a monomer during the polymerization of the microparticle would allow the EDTA to be incorporated into the polymer of the microparticle.

Alternatively, the polymerizable group may be linked directly to the EDTA group via esterification, without an intervening $CH_2$ group:

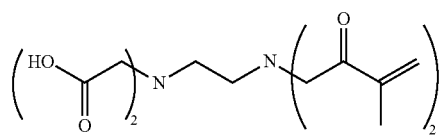

EDTA has many known derivatives, including EGTA, BAPTA and DOTA:

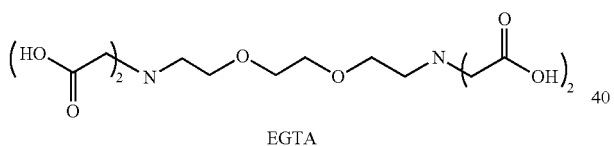
EGTA

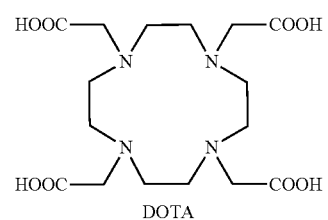
DOTA

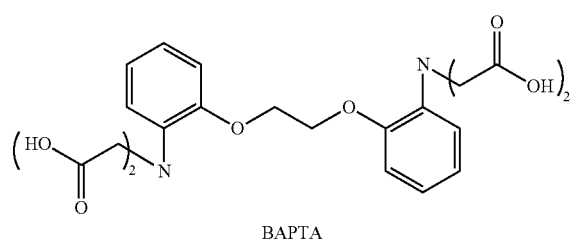
BAPTA

The following exemplary EDTA derivatives can chelate Re:

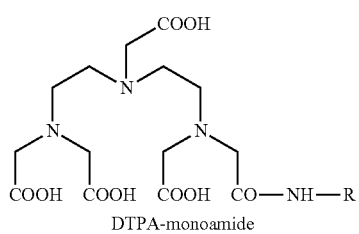
DTPA-monoamide

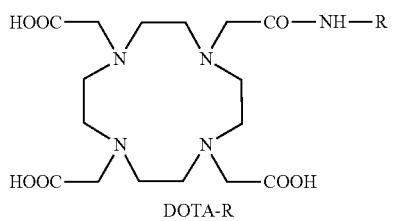
DOTA-R

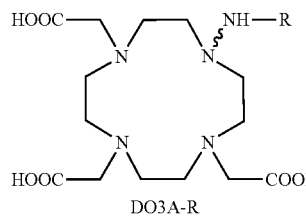
DO3A-R

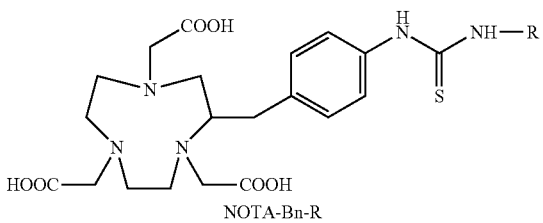
NOTA-Bn-R

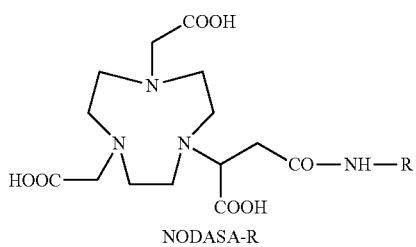
NODASA-R

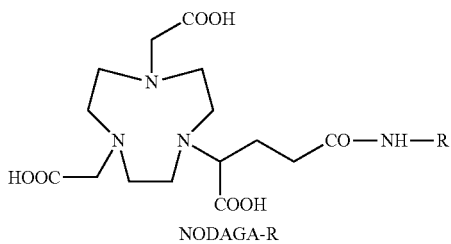
NODAGA-R

Attachment of a polymerizable group to an EDTA derivative, such as a methacrylate, via for example an ester or amide bond to one or more of the carboxylic acid groups of the derivative or as the R group, would allow for the use of a EDTA derivative chelating group to be associated with the microparticle:

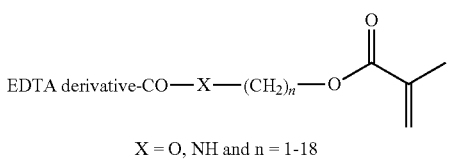

X = O, NH and n = 1-18

The use of such a monomer during the polymerization of the microparticle would allow the EDTA derivative to be incorporated into the polymer of the microparticle.

Alternatively, the polymerizable group may be linked directly to the EDTA derivative group via esterification or amidation, without an intervening $CH_2$ group:

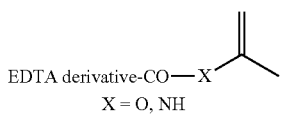

X = O, NH

In an embodiment, the chelating agent is the DOTA derivative of Compound A:

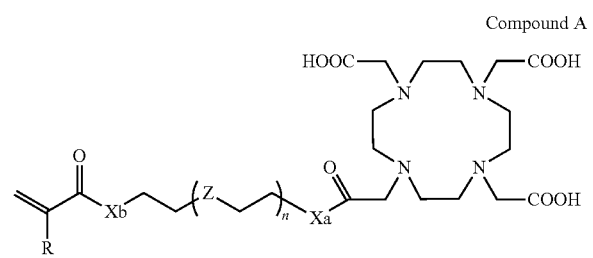

Compound A which contains a polymerizable group, wherein n may be between 0 and 16, inclusive; Xa and Xb may independently be O, S or N; Z may be C, O, S or N; and R may be alkyl or H. In certain embodiments, n is 1, Xa and Xb are O, and R is methyl. In other embodiments, n is 0. In further embodiments, n is between 0 and 10, inclusive; or is between 0 and 4, inclusive. The chelating agent may be incorporated into the microparticle during the polymerization of the particle as, for example, a monomer.

In some embodiments, the chelating agent is a DOTA derivative which is bound to the microparticle after the microparticle has been formed, via functionality present in the microparticle. For example, the microparticle may contain amine functionality, which may react with one or more of the acidic groups of DOTA:

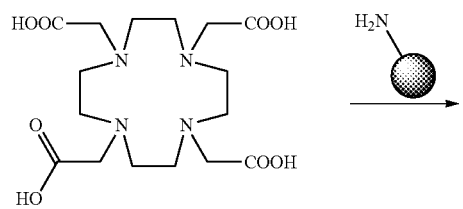

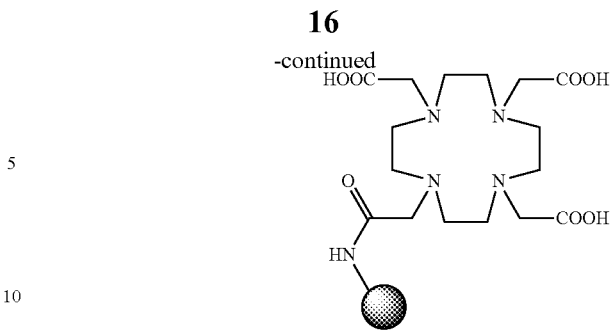

Derivatives of crown ethers may also be incorporated in the microparticle during or after polymerization of the microparticle as a chelating agent. As understood by a skilled artisan with the aid of the present disclosure, various sizes of crown ether rings may be used. In certain embodiments, the chelating agent is Compound B, a polymerizable benzo-18-crown-6:

Compound B

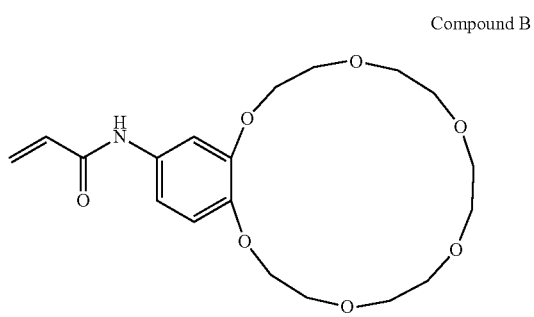 [SMILES: C=CC(=O)Nc1ccc2c(c1)OCCOCCOCCOCCOCCO2]

Non-limiting exemplary chelating agents which may be incorporated into the microparticle during the polymerization include those formed from iminodiacetic acid; styrene; butyl acrylate; glycidyl methacrylate; EDTA; aminocarboxylic acids such as alkylenediamine-N,N,N',N'-tetraacetic acid-(meth)acrylamide (MAM-EDTA); acrylic acid; butyl methacrylate; bromomethyl acrylate; α-chloromethacryloyl chloride; isonicotinyl hydrazone; 2-methacryloxy-5-methyl benzophenone; pyridoxal isonicotinyl hydrazone; peptides; oligomers; amino acids; phosphorodiamidate morpholino oligomers; dimercaptosuccinic acids; pentetic acid; mercaptoacetyltriglycine (MAG-3); hydroxyethylidine diphosphonate; 4-hexadecyl-2,2,9,9-tetramethyl-4,7-diaza-1,10-decanedithiol (HDD); an ethyl cysteinate dimer/lipiodol mixture; or a bis(diethyldithiocarbamato)nitrido (DEDC) chelator. These exemplary chelating agents are discussed in more detail below.

Chelating agents which may be incorporated into the microparticle during the polymerization include those formed from iminodiacetic acid, styrene, or butyl acrylate and glycidyl methacrylate. Iminodiacetic acid (IDA) may react with glycidyl methacrylate (GMA) either as a monomer or after polymerization of the glycidyl methacrylate, to form a GMA-IDA polymer (shown below).

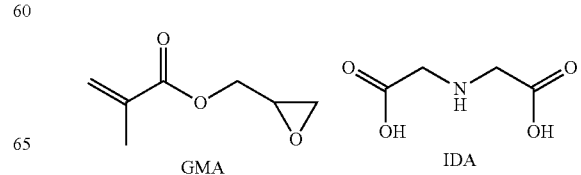

GMA    IDA

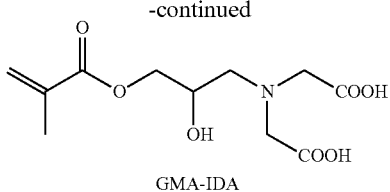

GMA-IDA

Copolymers of GMA may also be synthesized using styrene or butyl acrylate. The GMA-IDA-based copolymers may complex various metals, including Cd, Cu, Ni, Zn, and Co. One complexation scheme is shown below:

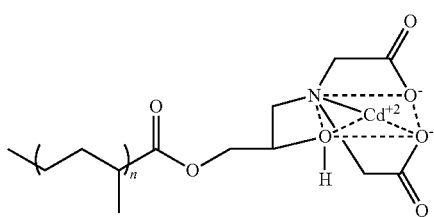

Chelating agents which may be incorporated into the microparticle also include those formed from aminocarboxylic acids such as alkylenediamine-N,N,N',N'-tetraacetic acid-(meth)acrylamide (MAM) and EDTA. EDTA may be added to a water-soluble polyallylamine in order to chelate rare earth metals, including Y, Er, Tm, Ho, and Dy. Another use includes the addition of chelating monomers of aminocarboxylic acids and HEMA (2-hydroxyethyl methacrylate), which can then complex with a metal ion. Two examples of this type of chelating monomer are:

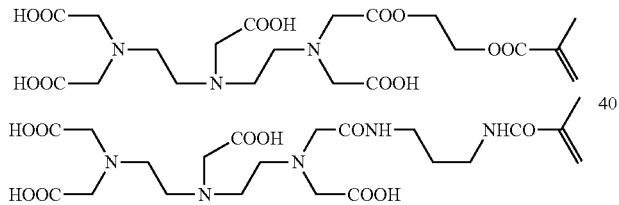

The presence of the methacrylate polymerizable group in the aminocarboxylic acids shown above allow for the use of a these compounds as a chelating group to be associated with the microparticle. The use of such a monomer during the polymerization of the microparticle would allow the aminocarboxylic acid derivative to be incorporated into the polymer of the microparticle.

MAM-EDTA monomers, such as the one shown below, are soluble in water and have an affinity for calcium ions. These are prepared from EDTA anhydride and hydroxylacrylamides, and the subsequent polymers may be resistant to hydrolysis.

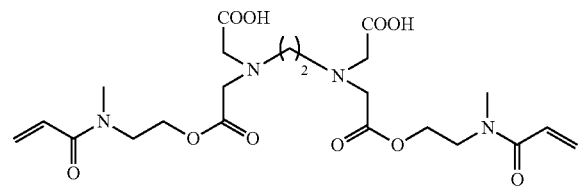

The presence of the methacrylamide polymerizable group in the MAM-EDTA monomers shown above allow for the use of a these compounds as a chelating group to be associated with the microparticle. The use of such a monomer during the polymerization of the microparticle would allow the MAM-EDTA derivative to be incorporated into the polymer of the microparticle Copolymers of acrylic acid, butyl acrylate, butyl methacrylate, styrene, iminodiacetic acid, bromomethyl acrylate, and/or α-chloromethacryloyl chloride can also be used as chelating agents.

Chelating agents which may be incorporated into the microparticle also include those formed from isonicotinyl hydrazone. A methacryloxy benzophenone-based polymer may be prepared using, for example, DVB as a crosslinking agent, then treated with isonicotinyl hydrazone. Exemplary monomers for these type of chelating agents, derived from 2-methacryloxy-5-methyl benzophenone and pyridoxal isonicotinyl hydrazone, are shown below.

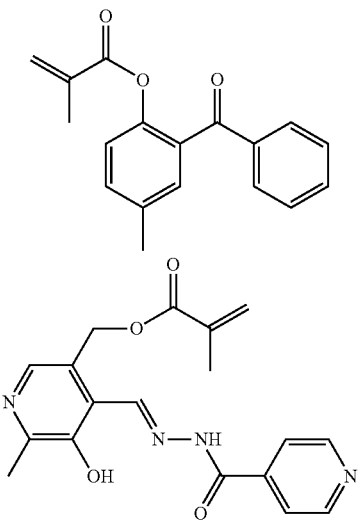

Similarly, phosphorodiamidate morpholino oligomers, dimercaptosuccinic acids, pentetic acid and MAG3, hydroxyethylidine diphosphonate, 4-hexadecyl-2,2,9,9-tetramethyl-4,7-diaza-1,10-decanedithiol (HDD), an ethyl cysteinate dimer/lipiodol mixture, and bis(diethyldithiocarbamato)nitrido (DEDC) chelators can be used, complexed with Re, Y, and/or I, for example.

These agents may contain chemical moieties, including heterocycles such as crown ethers, pyridine, imidazole, thiophene, thiazole, furan, purine, pyrimidine, hydroxyquinoline, metal-complexing dyes, and the like.

In an embodiment, the chelating agent is formed from iminodiacetic acid and glycidyl methacrylate.

In an embodiment, the chelating agent is present at between about 1% to about 20% by weight of the microparticle.

In certain embodiments, a microparticle is provided having the structure of Formula II:

$$P-X-M$$ Formula II wherein P is a polymer comprising polymerized monomers selected from at least one of the following: acrylates, acrylamides, acrylics, vinyls, acetals, allyls, cellulosics, methacrylates, polyamides, polycarbonates, polyesters, polyimides, polyolefins, polyphosphates, polyurethanes, silicones, styrenics, and polysaccharides;

wherein X represents Y-Z, wherein Z is a chelating group selected from at least one of the following: mercaptoacetyltriglycine (MAG-3), a mercaptoacetyltriglycine derivative; EDTA; an EDTA derivative including EGTA, BAPTA, DOTA, DTPA-monoamide, DO3A, NOTA-Bn, NODASA, and NODAGA; a crown ether, iminodiacetic acid; styrene; butyl acrylate; glycidyl methacrylate; aminocarboxylic acids such as alkylenediamine-N,N,N',N'-tetraacetic acid-(meth)acrylamide (MAM-EDTA); acrylic acid; butyl methacrylate; bromomethyl acrylate; α-chloromethacryloyl chloride; isonicotinyl hydrazone; 2-methacryloxy-5-methyl benzophenone; pyridoxal isonicotinyl hydrazone; peptides; oligomers; an amino acid; phosphorodiamidate morpholino oligomers; dimercaptosuccinic acids; pentetic acid; hydroxyethylidene diphosphonate; 4-hexadecyl-2,2,9,9-tetramethyl-4,7-diaza-1,10-decanedithiol (HDD); an ethyl cysteinate dimer/lipiodol mixture; and a bis(diethyldithiocarbamato)nitrido (DEDC) chelator;

wherein Y comprises a chain of between 1-18 non-hydrogen atoms independently selected from at least one of C, N, O or S; and wherein M is a radioisotope.

In an embodiment, the chelating group is incorporated into the microparticle during the polymerization of the particle as, for example, a monomer. The chelating group may contain a double bond, such as a methacryl or acryl moiety.

In certain embodiments, the chelating group is bound to the microparticle after the polymeric microparticle has been formed, via functionality present in the microparticle. For example, the microparticle may contain an amine or acid functional group, which may act as a handle to covalently bind to a chelating group such as MAG-3 or a MAG-3 derivative.

(iii) Radioisotopes

In some embodiments, the microparticles are associated with a radioisotope which is a β-emitter. In certain embodiments, the microparticles are associated with a radioisotope that is both a β- and γemitter. During decay of the β-particle, a neutron in the unstable nucleus is transformed into a proton, an electron and a neutrino. Additionally, energy is produced and released in the form of kinetic energy given to the electron and the neutrino. Passing through tissue, the ejected β-particles interact with other atoms and lose energy, leading to excited and ionized atoms. These activated species are responsible for therapeutic effects. During decay of the γparticle, energy is produced and released in the form of photons. These activated species are responsible for diagnostic effects, allowing for detection of the microparticles in vivo by, for example, a gamma camera.

The microparticles disclosed herein optionally contain transition metal, lanthanide, or group IIIA-IVA oxides, hydroxides, alkoxides, carboxylates, or combinations thereof, which have dimensions ranging from about 1 μm to about 2000 μm. Alternatively, the dimensions may range from about 1 μm to about 100 μm, or from about 10 μm to about 40 μm In certain embodiments, the radioisotope is rhenium, including $^{186}$Re and $^{188}$Re.

The association of the radioisotope within the polymer may be the result of either direct deposition of the radioisotope on or in the polymeric material, or a precipitation, reduction or oxidation process from a metal salt solution (e.g., a solution of metal halides, sulfonates, carboxylates, nitrates, or alkoxides) or a combination of any of these. Alternatively, the association of the particles of metals, metal cations and/or metal oxides within the polymer may be accomplished by performing the polymerization in the presence of a radioisotope-containing solution, suspension, or colloid.

In one embodiment, a radionuclide suitable for this application has an affinity for the chelating agent of the microparticle. This affinity may be conferred by incorporating the radioisotope in a suitable chemical species, such as a complex ion or colloid. An example of such a radioisotope is $^{186}$Re complexed with tin, which can be prepared, for example, by treating an aqueous solution of $^{186}$Re perrhenate with $SnCl_2$.

Rhenium is an element which is used in radiotherapy as its $^{186}$Re and $^{188}$Re isotopes. $^{186}$Re has a half-life of about 90 hours and decays with emission of a β-particle and a γparticle. $^{188}$Re has a half-life of about 17 hours and decays with emission of a β-particle and a γparticle, as well, but its β-particle has a higher maximum energy (approx. 2.12 MeV compared to 1.08 MeV). Thus, the rhenium radioisotopes may be useful for providing both diagnostic and therapeutic radiation.

Certain other radioisotopes in ionic forms may possess sufficient affinity for the microparticle; an example is $^{90}$Y as its $3^+$ ion. The β-emitting radioisotope may also emit γphotons that are detectable, for example, by a gamma camera, for imaging purposes. Suitable β-emitting radionuclides are selected from the group consisting of the lanthanides, yttrium, strontium, gold, phosphorus, and iridium. Radioactive palladium ($^{103}$Pd) and ytterbium ($^{169}$Yb) are also contemplated, although they emit soft x-rays, rather than β particles. In certain embodiments, the radionuclide is $^{90}$Y, $^{32}$P, $^{99m}$Tc, $^{111}$In, $^{67}$Ga, $^{166}$Dy, $^{201}$Th, $^{131}$I, $^{140}$La, $^{153}$Sm, $^{165}$Dy, $^{166}$Ho, $^{169}$Er, $^{175}$Yb, $^{177}$Lu, $^{186}$Re, $^{188}$Re, or combinations thereof.

Natural rhenium is composed of two isotopes, $^{185}$Re and $^{187}$Re, that form β-emitting $^{186}$Re and $^{188}$Re radioisotopes, respectively, upon neutron activation. The nuclear and dosimetric properties of the rhenium radioisotopes are comparable to those of $^{90}$Y, but they have imageable γphotons as well. Like the rhenium radioisotopes, $^{166}$Ho emits β-particles and γ-photons, as does $^{131}$I.

A radioactive polymer-based microparticle may be formed by contacting the polymer with a radioisotope, or by neutron activation of a polymeric material impregnated with a nonradioactive precursor isotope. The radioactivity may be incorporated during or after the fabrication of the polymer into microparticle form. In one embodiment, the radioisotope is neutron activated before associating with the polymer, to limit polymer degradation via neutron activation.

In one embodiment, the radioactivity may be provided by an $^{188}$W/$^{188}$Re generator to provide carrier-free $^{188}$Re as its $[^{188}ReO_4]^-$ anion.

The disclosed microparticles can readily be labeled with radioactivity at the point of use, such as at a hospital's radiopharmacy. This characteristic allows physicians to prescribe customized doses of radiation to the patient. The microparticles can be radiolabeled with an isotope intended for therapeutic purposes (e.g., a β-emitter) and/or imaging purposes (e.g., a γemitter). The microparticles described herein attract these species, facilitating proper dosing and minimizing undesirable radioactive waste.

The binding of the radioisotope may be measured, and in one embodiment, the radioisotope is not leached from the microparticle to an extent greater than about 3% of its original level by weight. In another embodiment, the radioisotope is not leached from the microparticle to an extent greater than about 1% of its original level by weight.

In an embodiment, the radioisotope is present in a range of between about 1% to about 30% by weight of the microparticle.

In certain embodiments, the microparticles may be associated with an additional imaging agent as well as a radioisotope. For example, the microparticles may comprise an MRI-detectable imaging agent (e.g., iron oxide) in addition to the association with a radioisotope. In some embodiments, the microparticles further comprise an iodinated MRI-detectable imaging agent.

III. Kits

The methods of the present disclosure may also be practiced using an embolization kit. Such kits may contain a microparticle in sterile form, and may include a sterile container of an acceptable reconstitution liquid, such as saline. Suitable reconstitution liquids are disclosed in Remington's Pharmaceutical Sciences and The United States Pharmacopia The National Formulary. Such kits may also include, if desired, other conventional kit components, such as, for example, one or more carriers, and/or one or more additional vials for mixing. Instructions, either as inserts or labels, indicating quantities of the embolic composition and carrier, guidelines for mixing these components, and protocols for administration may also be included in the kit. Sterilization of the containers and any materials included in the kit and lyophilization (also referred to as freeze-drying) of the embolic composition may be carried out using conventional sterilization and lyophilization methodologies known to those skilled in the art. In some embodiments, the lyophilized materials may be stored under vacuum or in an inert atmosphere.

Lyophilization aids useful in the embolization kits include but are not limited to mannitol, lactose, sorbitol, dextran, Ficoll, and polyvinylpyrrolidine (PVP). Stabilization aids useful in the embolization kits include but are not limited to ascorbic acid, cysteine, monothioglycerol, sodium bisulfite, sodium metabisulfite, gentisic acid, and inositol. Bacteriostats useful in the embolization kits include but are not limited to benzyl alcohol, benzalkonium chloride, chlorobutanol, and methyl, propyl or butyl paraben. A component in an embolization kit can also serve more than one function. For example, a reducing agent can also serve as a stabilization aid, a buffer can also serve as a ligand, and a lyophilization aid can also serve as an ancillary or co-ligand.

The absolute and relative amounts of each component of an embolization kit are determined by a variety of considerations that are in some cases specific for that component and in other cases dependent on the amount of another component or the presence and amount of an optional component. In general, the minimal amount of each component is used that will give the desired effect of the formulation. The desired effect of the formulation is that the end-user of the embolization kit may practice the embolization methods of the invention with a high degree of certainty that the subject will not be harmed.

The embolization kits may also contain written instructions for the practicing end-user. These instructions may be affixed to one or more of the vials or to the container in which the vial or vials are packaged for shipping or may be a separate insert, termed the package insert.

The present disclosure provides a kit for performing a prophylactic or therapeutic treatment of a mammal. The kit may include a sterile container and sterile and biocompatible polymeric microparticles capable of being associated with a radioisotope. In another embodiment, the kit for performing a prophylactic or therapeutic treatment of a mammal comprises a needle or a catheter; means for injecting a liquid based composition through said needle or catheter; and sterile polymeric microparticles capable of being associated with a radioisotope. In one embodiment, the microparticles of the kit may be already associated with a radioisotope. In this regard, the various embodiments of the microparticles disclosed herein are also encompassed by the present invention's kit.

IV. Methods

The present disclosure also relates to a method of preparing a radioisotope-labeled microparticle, comprising the steps of: 1) fabricating a microparticle, and 2) associating the resulting microparticle with a radioisotope.

Another aspect of the present disclosure relates to a method of treating a mammal suffering from a medical condition, comprising the step of administering to said mammal a therapeutically effective amount of radioactive microparticle comprising a monomer, chelating agent and a radioisotope.

A further aspect of the present disclosure relates to processes of chelating a radioactive transition-metal, lanthanide or Group 13-14 metal particle with the polymeric material. In one embodiment, the process involves a radioisotope which is chelated to the polymerized monomer. In one embodiment, the chelating process may involve a chelation agent which is short enough to remain soluble in water yet long enough to chelate the appropriate radioisotope. For example, the chelating agent may contain a backbone chain of 4-18 non-hydrogen atoms, including carbon, oxygen and nitrogen atoms. The chelating agent may be partially or fully cyclic or heterocyclic, such as including a crown ether, pyridine or imidazole rings. The types of chelating agents vary, and they may be in their conjugate base form at around physiological pH.

In certain embodiments, the process of chelating involves a chelating agent which is linked to the microparticle after polymerization of the microparticle monomers. Alternatively, the process of chelating involves a chelating agent which is incorporated into the microparticle during the polymerization, i.e. where the chelating agent is a monomer. In certain embodiments, the chelating agent may be introduced into the polymer in a separate step (e.g., by a grafting or coupling reaction).

Accordingly, radioactive transition-metal, lanthanide or Group 13-14 metal particles can be chelated with a polymeric material by contacting the polymeric material with a radioisotope solution for a time and at a temperature sufficient to chelate the isotope with the polymeric material. In one embodiment, the process involves an isotope intended for therapeutic purposes (e.g., a β-emitter) and for imaging purposes (e.g., a γ emitter). In one embodiment, the process involves a radioisotope provided by a $^{188}W/^{188}Re$ generator to provide carrier-free $^{188}Re$ as its $[^{188}ReO_4]^-$ anion, which may be chelated with the polymeric material. In certain embodiments, the polymeric material also is associated with an imaging agent in addition to a radioisotope, such as a MRI-detectable imaging agent comprising iodine.

Another process of chelating radioisotopes with the polymeric material comprises adding the radioisotope or its corresponding salt solution or colloid into the initial polymerization solution or suspension for the polymeric material. In such a polymerization/association process, there is preferably no change in the polymerization process for the polymeric material itself. Therefore, any polymerization process that produces a polymeric material can be incorporated into the process of the present disclosure by adding a radioisotope solution, colloid, or suspension into the initial polymerization solution or suspension.

The process of chelating radioisotopes may be measured. In one embodiment, the process of chelating a radioisotope results in a radioisotope-labeled microparticle wherein the radioisotope is not leached from the microparticle to an extent greater than about 10% of its original level by weight over a specific amount of time, such as one month, three months, six months or a year. In another embodiment, the process of chelating a radioisotope results in a radioisotope-labeled microparticle wherein the radioisotope is not leached from the microparticle to an extent greater than about 3% of its original level by weight over one month, three months, six months or a year. In a further embodiment, the process of chelating a radioisotope results in a radioisotope-labeled microparticle wherein the radioisotope is not leached from the microparticle to an extent greater than about 1% of its original level by weight over one month, three months, six months or a year.

Another aspect of the present disclosure relates to processes of associating radioactive transition-metal, lanthanide or Group 13-14 metal particles with the polymeric material. The association process may be accomplished in at least three ways. First, the particles can be associated with, or precipitated in the pores of, the polymeric materials via a chemical reaction. Second, the particles can be deposited on and/or within the polymeric material through direct contact between the material and a solution or suspension of the particles. Third, the radioisotope-containing polymeric material can be produced by introducing a radioisotopic salt solution, suspension, or colloid into the initial polymerization solution or suspension of the polymeric material, or after the initial polymerization, to associate with the chelating agent. In all three methods, the metal particles are associated with the polymeric materials or within the pores thereof, enabling the detection and control of such materials in implantation applications. The various polymeric materials mentioned above are suitable for the association processes described herein.

Accordingly, radioactive transition-metal, lanthanide or Group 13-14 metal particles can be associated with a polymeric material by contacting the polymeric material with a radioisotopic salt solution for a time and at a temperature sufficient to bind, associate, reduce, oxidize, or precipitate the isotopic salt into isotope-containing particles that are deposited on or within the polymeric material. In certain embodiments, the polymeric material is porous and the process enables the porous materials to comprise at least part of the metal particles within the pores of the material. In such cases, the sizes of the metal particles may either be larger or smaller than the sizes of the pores of the material, as measured by the cross-sections of the pores.

Another process of associating radioisotopes with the polymeric material comprises adding the radioisotopic particles or their corresponding salt solution or colloid into the initial polymerization solution or suspension for the polymeric material. In an embodiment, the resultant polymeric material is porous and the process enables the porous materials to comprise at least part of the radioisotopes within the pores of the material. In such a polymerization/association process, there is preferably no change in the polymerization process for the polymeric material itself. Therefore, any polymerization process that produces a polymeric material can be incorporated into the process of the present invention by adding a radioisotopic salt solution, colloid, or suspension into the initial polymerization solution or suspension.

In one embodiment, the process involves an isotope intended for therapeutic purposes (e.g., a β-emitter) and for imaging purposes (e.g., a γemitter). In one embodiment, the process involves a radioisotope provided by a $^{188}W/^{188}Re$ generator to provide carrier-free $^{188}Re$ as its $[^{188}ReO_4]^-$ anion, which may be associated with the polymeric material. In certain embodiments, the process involves an imaging agent in addition to a radioisotope, such as a MRI-detectable imaging agent comprising iodine.

The process of associating radioisotopes may be measured. In one embodiment, the process of associating a radioisotope results in a radioisotope-labeled microparticle wherein the radioisotope is not leached from the microparticle to an extent greater than about 10% of its original level by weight over a specific amount of time, such as one month, three months, six months or a year. In another embodiment, the process of associating a radioisotope results in a radioisotope-labeled microparticle wherein the radioisotope is not leached from the microparticle to an extent greater than about 3% of its original level by weight over one month, three months, six months or a year. In a further embodiment, the process of associating a radioisotope results in a radioisotope-labeled microparticle wherein the radioisotope is not leached from the microparticle to an extent greater than about 1% of its original level by weight over one month, three months, six months or a year.

The microspheres may be administered to the patient through the use of syringes or catheters either alone or in combination with vasoconstricting agents or by any other means of administration that effectively causes the microspheres to become embedded in, for example, cancerous or tumor-bearing tissue.

For purposes of administration, the microspheres may be suspended in a biocompatible fluid medium. The medium may have a sufficient density or viscosity that slows or prevents the microspheres from settling out of suspension during the administration procedure. The medium may also be sufficiently opaque to be detectable by x-ray imaging (i.e., radiopaque) to allow visualization of the injection. Exemplary liquid vehicles for suspension of the microspheres include aqueous sodium chloride at 0.9% concentration by weight, polyvinylpyrrolidone (PVP), sold under the trade designation Plasdone K-30 and Povidone by GAF Corp, contrast media sold under the trade designation Visipaque or Omnipaque by Amersham Biosciences of Uppsala, Sweden; contrast media sold under the trade designation Optiray by Mallinckrodt, Inc, of St. Louis, Mo., contrast media sold under the trade designation Metrizamide by Nyegard & Co. of Oslo, Norway; contrast media sold under the trade designation Renografin 76 by E. R. Squibb & Co., 50% dextrose solutions and saline.

The radiolabeled microspheres may also be administered to a patient in combination with agents that enhance the efficacy of radiotherapy, such as radiosensitizers. Without being bound by theory, radiosensitizers are believed to enhance the therapeutic effect of radiation by either amplifying the damage to cells by the radiotherapy, or by inhibiting radiation-damaged cells from multiplying or repairing themselves. Examples of radiosensitizers include gemcitabine, docetaxel, and nitrated imidazoles, such as metronidazole and nimorazole.

The specific examples included herein are for illustrative purposes only and are not to be considered as limiting to this disclosure. Any agents and reagents used in the following examples are either commercially available or can be prepared according to standard literature procedures by those skilled in the art of organic synthesis.

EXAMPLE 1

Synthesis of MAG-3 Chelating Group (Compound 4)

The MAG-3 group (Compound 4) was synthesized via the following synthetic route:

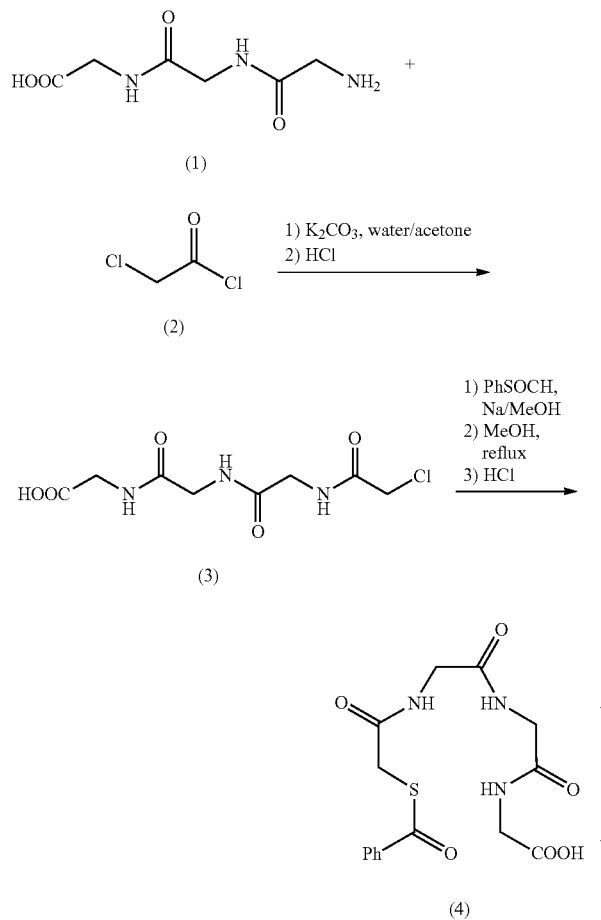

To a suspension of Compound 1 (H-Gly-Gly-Gly-OH; 30 gm) in 200 mL water and 200 mL acetone, was added potassium carbonate (44 gm). The mixture was cooled to 0° C. and chloroacetyl chloride (Compound 2; 15.1 mL) was added dropwise, and the mixture was stirred at 0° C. for 1.5 hr. The acetone was removed under reduced pressure and the resultant solution was acidified at 0° C. with 12N HCl, then allowed to stand at 4° C. for 2 hr. The precipitate was collected in a Buchner funnel, rinsed with water and acetone, then dried under vacuum to provide 26.9 gm (64% yield) of Compound 3 as a white solid. $^1$H NMR (400 mHz; DMSO-$d_6$): δ; 12.5 (br. s., 1H), 8.4 (t, 1H), 8.3 (t, 1H), 8.2 (t, 1H), 4.1 (s, 2H), 3.8 (m, 6H).

A solution of sodium (7.8 gm) in methanol (300 mL) was cooled to 0° C. and thiobenzoic acid (46.5 mL) was added. A suspension of Compound 3 (30 gm) in methanol (1 L) was added to the solution, and the mixture was refluxed for 4 hr, then stirred at ambient temperature for an additional 12 hr. The methanol was removed under reduced pressure to provide a residue, to which was added 300 mL of 2N HCl and which was then stirred for 1 hr. The precipitate was filtered (Buchner funnel), washed with water and chloroform, and dried to provide Compound 4 (36.9 gm, 89% yield) as a pink solid. The crude material was purified by dissolution in a mixture of warm methanol/water (8/2) to provide material of >95% purity by HPLC at 240 nm. $^1$H NMR (400 mHz; DMSO-$d_6$): δ; 12.6 (br. s, 1H); 8.5 (t, 1H), 8.2 (dt, 2H), 7.9 (d, 2H), 7.7 (t, 1H), 7.6 (t, 2H), 3.9 (s, 2H), 3.8 (m, 6H). MS ESI (m/z): MH+368.1, 735.3; M−366.1, 733.3.

EXAMPLE 2

Synthesis of O-linked MAG-3 Ligand

The MAG-3 chelating group (Compound 4) was linked to a methacryloyl polymerizable group (Compound 8) by an ester linkage from Compound 4 via the following synthetic route:

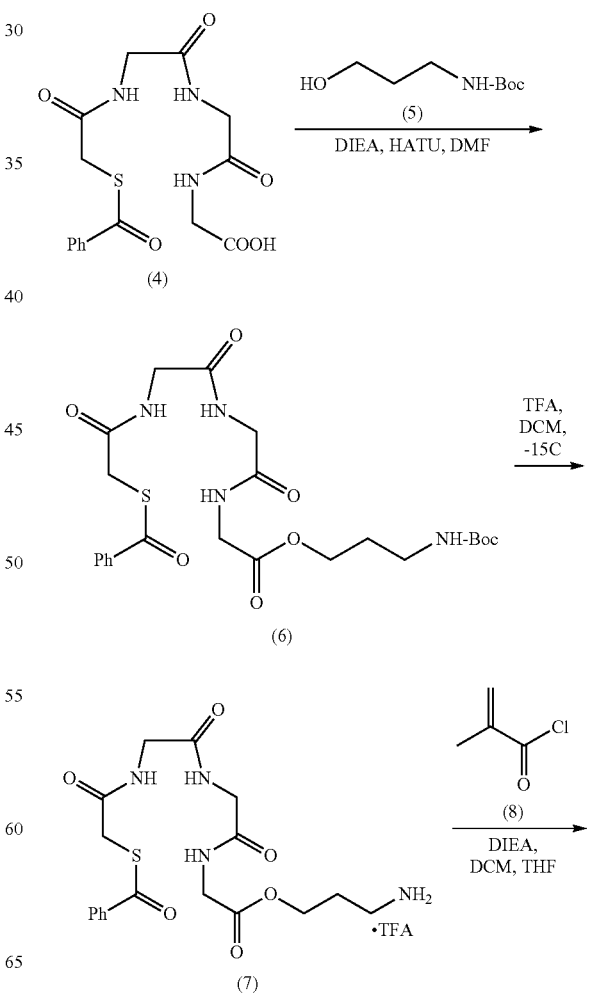

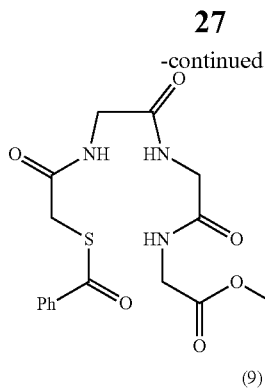

(9)

Into a mixture of 3-(BOC-amino)-1-propanol (Compound 5; 9.8 mL) and DIEA (19 mL), was added a solution of Compound 4 (20 gm) in DMF (144 mL). The mixture was cooled to 0° C. and, with stirring, HATU (21.7 gm) was added, then the solution was stirred for 1 hr at 0° C. and further stirred at ambient temperature for 12 hr. The DMF was removed under reduced pressure, and the residue was triturated with a mixture of diethyl ether and ethyl acetate (1:1) for 12 hr. The solid obtained was collected in a Buchner funnel, triturated with acetonitrile for 12 hr, then filtered again through a Buchner funnel to provide Compound 6 (22 gm, 79% yield) as a maroon solid of 90% purity by HPLC (254 nm). $^1$H NMR (400 mHz; DMSO-$d_6$): δ; 8.5 (t, 1H), 8.3 (m, 2H), 7.9 (m, 2H), 7.7 (t, 1H), 7.6 (t, 2H), 6.9 (t, 1H), 4.0 (m, 2H); 3.9 (s, 2H), 3.7-3.8 (m, 6H), 3.0 (m, 2H), 1.7 (m, 2H), 1.4 (s, 9H). MS ESI (m/z): MH+525.3, 425.2; M−569.4, 523.3, 362.2.

To a solution of Compound 6 (1 gm) in anhydrous DCM (4 mL), cooled to −15° C., was added TFA (2.9 mL) dropwise. After 2 hr at −10° C., diethyl ether was added to form a precipitate, which was collected in a Buchner funnel and washed with diethyl ether. The product was lyophilized to provide the TFA salt of Compound 7 (590 mg, 59% yield) as a white solid of approx. 70-90% purity. $^1$H NMR (400 mHz; DMSO-$d_6$): δ; 8.5 (m, 1H), 8.3 (m, 2H), 7.9 (m, 2H), 7.7 (m, 3H), 7.6 (t, 2H), 4.1 (m, 2H); 3.9 (s, 2H), 3.7-3.8 (m, 8H), 2.9 (m, 2H), 1.9 (m, 2H).

To a cooled (0° C.) suspension of Compound 7/TFA (990 mg) in a mixture of DCM/THF (10 mL/10 mL) was added dropwise first methacrylolyl chloride (Compound 8; 2.7 mL), and then DIEA (5 mL). The reaction mixture was stirred at 0° C. for 2.5 hr, then concentrated under reduced pressure to provide the product, which was purified via silica gel chromatography (DCM/MeOH 97/3) to provide Compound 9 (250 mg, 27% yield) as a beige solid of >95% purity. $^1$H NMR (400 mHz; DMSO-$d_6$): ppm δ; 8.5 (m, 1H), 8.2 (m, 2H), 7.9 (m, 3H), 7.7 (m, 1H), 7.6 (t, 2H), 5.6 (s, 1H), 5.3, (s, 1H), 4.1 (t, 2H); 3.9 (s, 2H), 3.8-3.9 (m, 6H), 3.2 (m, 2H), 1.9 (s, 3H), 1.8 (t, 2H).

EXAMPLE 3

Synthesis of N-linked MAG-3 Ligand

In a similar manner, the MAG-3 chelating group (Compound 4) was linked to a methacryloyl group by modifying the ester group of Compound 4 into an amide group, via the following synthetic route:

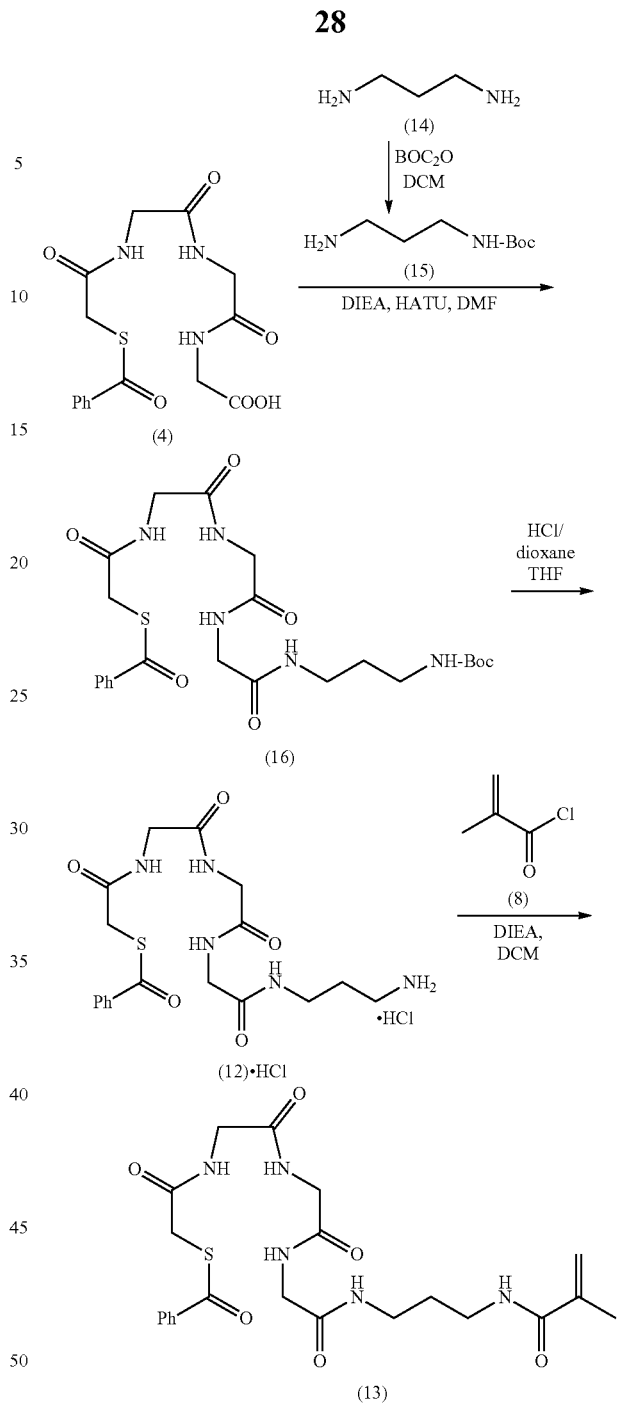

Compound 15 was synthesized in the following manner. Under argon, a solution of Boc$_2$O (30 gm) in DCM (160 mL) was added dropwise to a solution of 1,2-propanediamine (Compound 14; 18.4 mL) and triethylamine (114 mL) in DCM (330 mL). The reaction mixture was stirred at ambient temperature overnight. The solution was neutralized with 2N sodium bicarbonate (150 mL) and extracted with DCM (2×). The organic phases were combined, dried over sodium sulfate and evaporated under reduced pressure to provide a white solid, which was purified over silica gel (DCM/MeOH 9:1 then DCM/MeOH/Et$_3$N 8:8:1) to provide Compound 15 (13 gm, 59% yield) as a colorless oil. $^1$H NMR (400 mHz; CDCl3): δ; 4.9 (br. s, 1H), 3.2 (m, 2H); 2.7 (t, 2H), 1.6 (m, 2H), 1.5 (m, 11H).

To a solution of Compound 4 (26.8 gm) in DMF (260 mL) was added HATU 929.1 gm) and DIEA (12.3 mL). The solution was stirred for 10 min, at which time a solution of Compound 15 (14 gm) in DMF (50 mL) was added. The solution was stirred at room temperature overnight. DCM (200 mL) was added and the solid was filtered (Buchner funnel) and triturated twice with acetonitrile (250 mL), to provide Compound 16 (35.2 gm, 92% yield) as a pale pink solid with a 96% purity at 245 nm. $^1$H NMR (400 mHz; DMSO-$d_6$): δ; 8.5 (t, 1H), 8.2 (t, 1H), 8.1 (t, 1H), 7.9 (d, 2H), 7.7 (m, 2H), 7.6 (t, 2H), 6.8 (m, 1H), 3.9 (s, 2H), 3.8 (m, 5H), 3.7 (d, 2H), 2.9 (m, 2H), 2.7 (m, 2H), 1.5 (m, 2H), 1.4 (s, 9H). MS ESI (m/z): MH+524.3, 424.3; M–568.3, 522.3, 361.2.

A solution of 4N HCl in dioxane (186 mL) was added to a 40° C. solution of Compound 16 (48.6 gm) in THF (600 mL). The reaction mixture was stirred at 40° C. overnight, then chilled at 0° C. for 1 hr. The resulting precipitate was filtered (Buchner) and triturated with 400 mL acetonitrile to provide Compound 12 as an HCl salt (37.1 gm, 87% yield) of approx. 85-90% purity. The solid was dissolved in water, filtered, and lyophilized to provide Compound 12 as the HCl salt (30.2 gm, 70% yield) of >98% purity by HPLC (254 nm) as a white solid. $^1$H NMR (400 mHz; DMSO-$d_6$): δ; 8.6 (m, 1H), 8.3 (m, 1H), 8.2 (m, 1H), 7.9-8.0 (m, 5H), 7.7 (m, 1H), 7.6 (t, 2H), 3.9 (s, 2H), 3.7-3.8 (m, 4H), 3.7 (d, 2H), 3.1 (m, 2H), 2.7 (m, 2H), 1.7 (m, 2H). MS ESI (m/z): MH+424.2; M–468.2, 261.1.

To a cooled (0° C.) suspension of Compound 12/HCl (14.4 gm) in 350 mL of DCM was added dropwise methacrylolyl chloride (Compound 8; 15.1 mL) and DIEA (27.3 mL). The reaction mixture was stirred at 0° C. for 3 hr, then warmed to ambient temperature and the solid was collected with a Buchner funnel. The product was washed with 150 mL water and dried to a light pink solid with a purity of approx. 80-90%. The solid was triturated with acetonitrile (120 mL) for 1 hr, filtered, and resuspended in 100 mL of DMSO with heating to 120° C. to achieve full dissolution. A solid precipitated with cooling, was filtered and rinsed with acetonitrile and dried under vacuum. Compound 13 (5.4 gm; 35% yield) was obtained as a pale pink solid with a purity of approx. 90% purity by HPLC (265 nm). $^1$H NMR (400 mHz; DMSO-$d_6$): δ; 8.5 (t, 1H), 8.3 (t, 1H), 8.2 (t, 1H), 7.9-8.0 (m, 3H), 7.7 (m, 2H), 7.6 (t, 2H), 5.6 (s, 1H), 5.3 (s, 1H), 3.9 (s, 2H), 3.7-3.8 (m, 4H), 3.7 (d, 2H), 3.1 (m, 4H), 1.9 (s, 3H), 1.6 (m, 2H). MS ESI (m/z): MH+492.4; M–329.2.

As the coupling of methacrylolyl chloride (Compound 8) with Compound 12/HCl was low-yielding, an alternative, more convergent route to Compound 13 was derived, as shown in the following scheme:

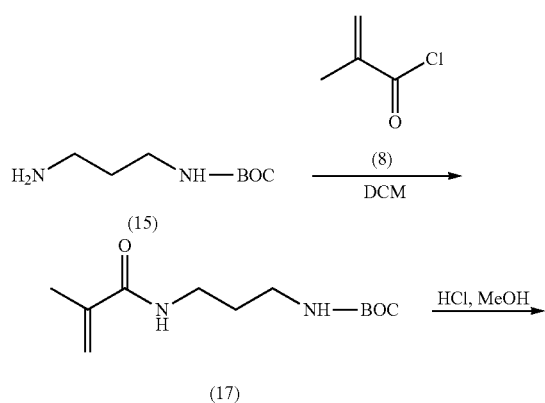

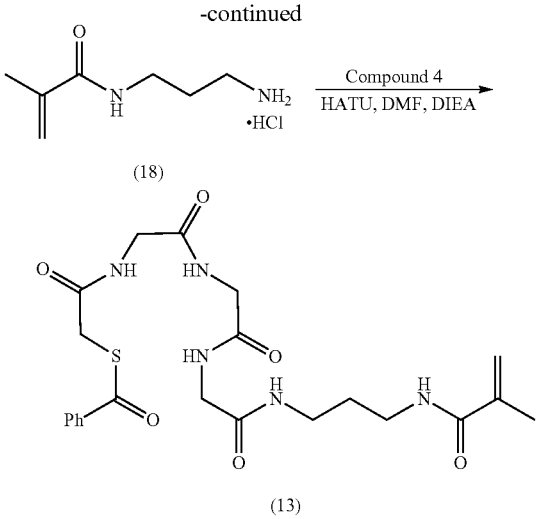

To a solution of Compound 15 (3.9 gm) in anhydrous DCM (40 mL) was added methacryloyl chloride (Compound 8; 4.4 mL). The reaction mixture was stirred at ambient temperature for 18 hr. A solution of 2N sodium bicarbonate was added and the mixture extracted with DCM (3×). The combined organic phases were dried over sodium sulfate, filtered and concentrated under reduced pressure. The product was purified over silica gel (DCM, then DCM/MeOH 97/3) to provide Compound 17 (2.7 gm, 50% yield) as a white solid of approx. 98% purity by HPLC (254 nm). $^1$H NMR (400 mHz; DMSO-$d_6$): ppm δ; 7.9 (m, 1H), 6.8 (m, 1H), 5.6 (s, 1H), 5.3 (s, 1H), 3.1 (m, 2H), 2.9 (m, 2H), 1.9 (m, 3H), 1.5 (t, 2H), 1.4 (s, 9H). MS ESI (m/z): MH+243.1, 187.1, 126.1; M–287.2.

To a solution of Compound 17 (10.5 gm) in 30 mL of MeOH at room temperature was added a solution of 4N HCl/dioxane (21.7 mL), and the mixture was stirred for 16 hr. The solution was concentrated under reduced pressure and the solid was triturated with 80 mL of toluene. After filtration (Buchner), Compound 18 (7.5 gm, 96% yield) was obtained as a white solid. $^1$H NMR (400 mHz; DMSO-$d_6$): ppm δ; 8.2 (m, 1H), 8.0 (m, 3H), 6.3 (br. s), 5.7 (s, 1H), 5.3 (s, 1H), 3.2 (m, 2H), 2.8 (m, 2H), 1.9 (s, 3H), 1.7 (m, 2H).

To a solution of HATU (11.9 gm) and DIEA (5.2 mL) was added a solution of Compound 4 (11 gm) in 120 mL DMF. After stirring for 10 min, a solution of Compound 18 (5.88 gm), DIEA (5.2 mL) and a catalytic amount of phenothiazine in DMF (24 mL) was added. The reaction was monitored by HPLC after 16 hr but found to not have undergone complete conversion, so an additional amount of HATU (7 gm) and a solution of Compound 18 (8.9 gm), DIEA (8.7 mL) in DMF (30 mL) was added. The mixture was stirred for an additional 16 hr. After addition of DCM (100 mL), the solid was filtered (Buchner) and triturated twice with acetonitrile (150 mL) to provide Compound 13 (13.7 gm, 92% yield) as a pale pink solid of approx. 95% purity (265 nm). $^1$H NMR (400 mHz; DMSO-$d_6$): δ; 8.5 (t, 1H), 8.3 (t, 1H), 8.2 (t, 1H), 7.9-8.0 (m, 3H), 7.7 (m, 2H), 7.6 (t, 2H), 5.6 (s, 1H), 5.3 (s, 1H), 3.9 (s, 2H), 3.7-3.8 (m, 4H), 3.7 (d, 2H), 3.1 (m, 4H), 1.9 (s, 3H), 1.6 (m, 2H). MS ESI (m/z): MH+492.4; M–329.2.

Linking MAG-3 to a Microparticle

The MAG-3 chelating group may be linked to a microparticle by at least two general approaches: (1) by addition of a polymerizable group to the chelating group via the linker, and formation of the microparticle by polymerization (e.g., in the presence of other polymerizable monomers), or (2) by forming a microparticle separately, then coupling the chelating group via a linker to the microparticle after the material has been initially polymerized. Examples of these general approaches are shown below:

Approach 1:

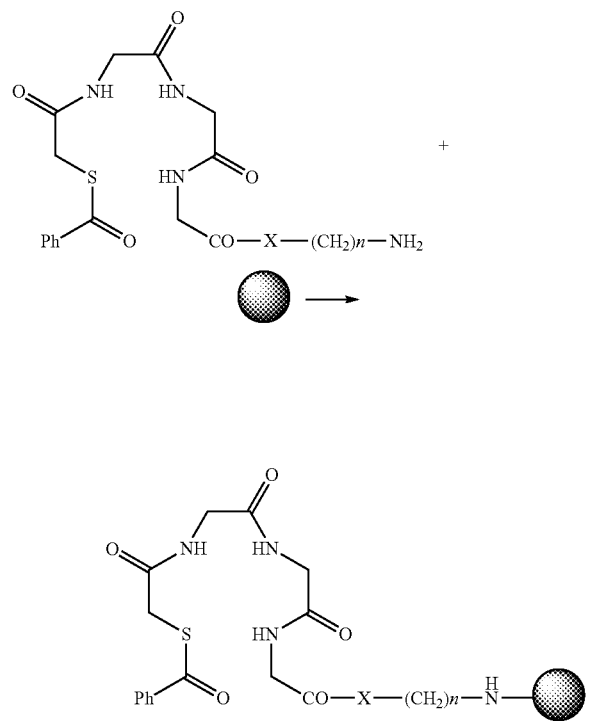

Approach 2:

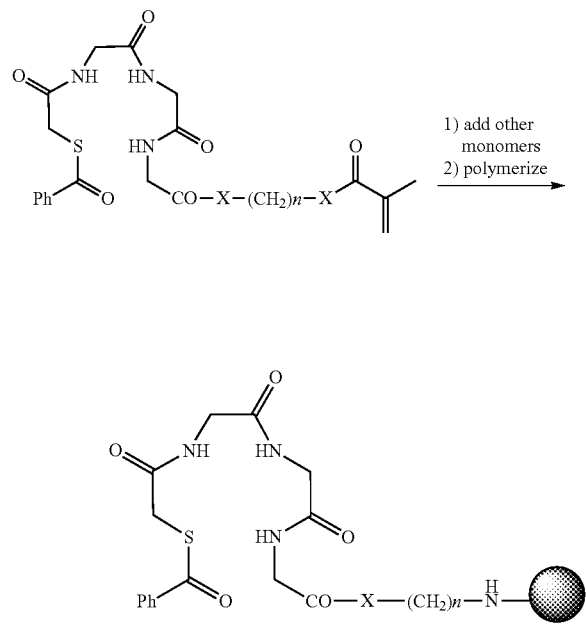

EXAMPLE 4

An Example of Approach 1

An example of Approach 1 is shown in the following scheme:

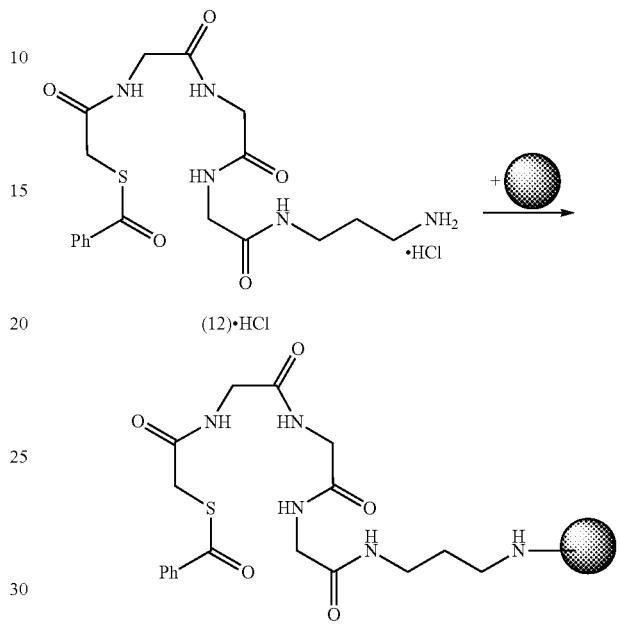

A water/oil emulsion-suspension-polymerization method was used to prepare microspheres using sodium acrylate and N-tris-hydroxy-methyl methylacrylamide monomers. In this method, 6.75 gm of N,N-methylene-bis-acrylamide, 25.18 gm of N-tris-hydroxy-methyl methylacrylamide, and 2.2 gm of sodium acrylate (97%) were added to 250 mL of an acetate buffer (prepared with 58 gm NaCl, 27.2 gm sodium acetate, 400 mL water and 300 mL glycerin, with the pH adjusted to 6.0 with acetic acid) at 50° C. The pH of the aqueous phase was adjusted with 50% aqueous acetic acid to maintain the pH at 6.0. The aqueous phase was filtered and an ammonium persulfate solution (0.34 gm of ammonium persulfate in 5 mL of water) was added. An emulsion was formed by dispersing the water phase into the oil phase at 60° C. with a mechanical stirrer at 288 rpm. One mL of TEMED (N,N,N',N'-tetraethylmethylenediamine) was added to catalyze the reaction. The emulsion was stirred for 90 minutes. When the polymerization reaction was completed, deionized water was added and the suspension was centrifuged at 3500 rpm for 5 minutes. Microspheres were separated from the supernatant and washed 4 times with deionized water. Microspheres were acidified at pH 1.5 with HCl 1N and washed 6 times with deionized water.

A sample of the microspheres were suspended in 0.9% aqueous NaCl for granulometry analysis (Ellix software). The results showed that the diameter of the microspheres ranged from between about 27.26 μm and about 140.34 μm, with a mean diameter of about 73.71 μm.

The morphology of the microspheres was evaluated after lyophilization of the microspheres, using an optical microscope linked to a computer for analysis of the images. The microscopy results for the microspheres of Example 4 after lyophilization are shown in FIG. 1. As shown in the image, the microspheres formed in Example 4 are substantially spherical.

Coupling of the Microparticles of Example 4 with MAG-3 Ligand

The following two procedures were used for grafting or coupling the MAG-3 ligand to the microparticles of Example 4.

In the first procedure, dry microspheres (250 mg) were dispersed in 3.6 mL of DMF solvent. The DIEA (52.5 mg) and the HCl salt of Compound 12 (98 mg) were added to the slurry. The suspension was placed in an ice bath and HATU (81 mg) was added to the suspension at 0° C., whereupon the suspension turned fluorescent yellow. The suspension was kept at 0° C. for 1 hour and at room temperature for 19 hours. The microspheres were separated from the supernatant and washed 4 times with deionized water.

In the second procedure, dry microspheres (250 mg) were dispersed in 3.6 mL of DMF solvent. The DIEA (52.5 mg) was added to the slurry. The suspension was placed in an ice bath and HATU (81 mg) was added to the suspension at 0° C. Two minutes after the HATU addition, the HCl salt of Compound 12 (98 mg) was added, whereupon the suspension turned ocher yellow. The suspension was kept at 0° C. for 1 hour and at room temperature for 19 hours. The microspheres were separated from the supernatant and washed 4 times with deionized water.

The morphology of a sample of the microspheres from each procedure was evaluated before and after sonication, which disperses microparticle aggregates, using an optical microscope linked to a computer for analysis of the images.

Figure 2:
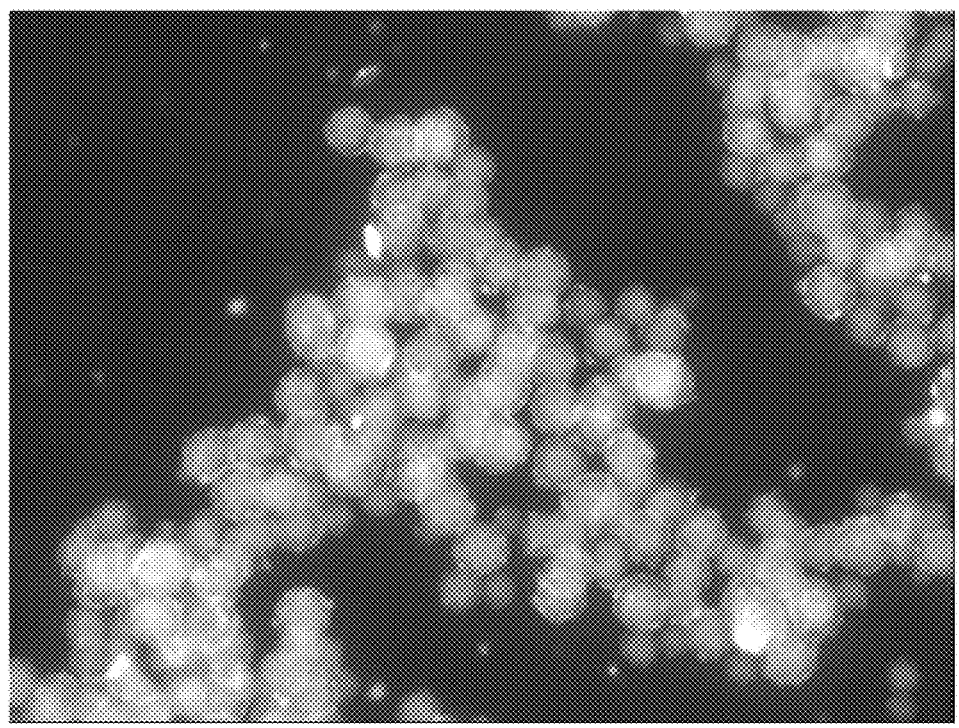
FIG. 2 is a microscope image of microparticles of Example 4 after the first procedure for coupling to a chelating agent and prior to sonication.
Figure 3:
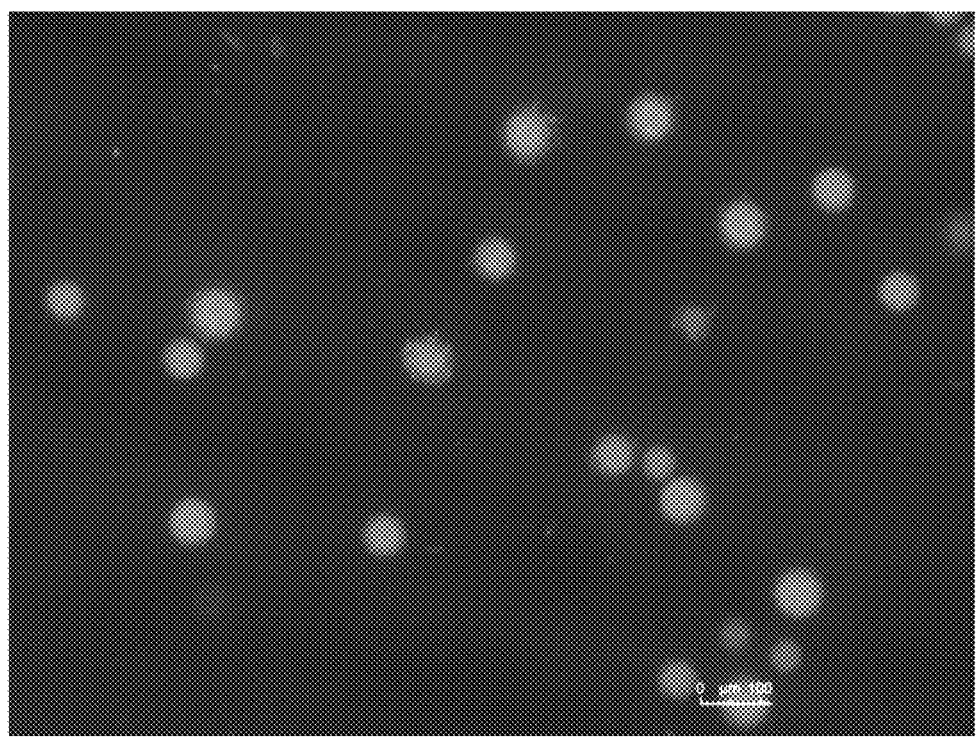
FIG. 3 is a microscope image of microparticles of Example 4 after the first procedure for coupling to a chelating agent and after sonication.

The microscopy results for the microspheres of the first procedure of Example 4 before sonication are shown in FIG. 2. The microscopy results for the microspheres of the first procedure of Example 4 after sonication are shown in FIG. 3. As shown in the images, the microspheres formed by coupling of the microspheres of Example 4 with MAG-3 are substantially spherical.

Figure 4:
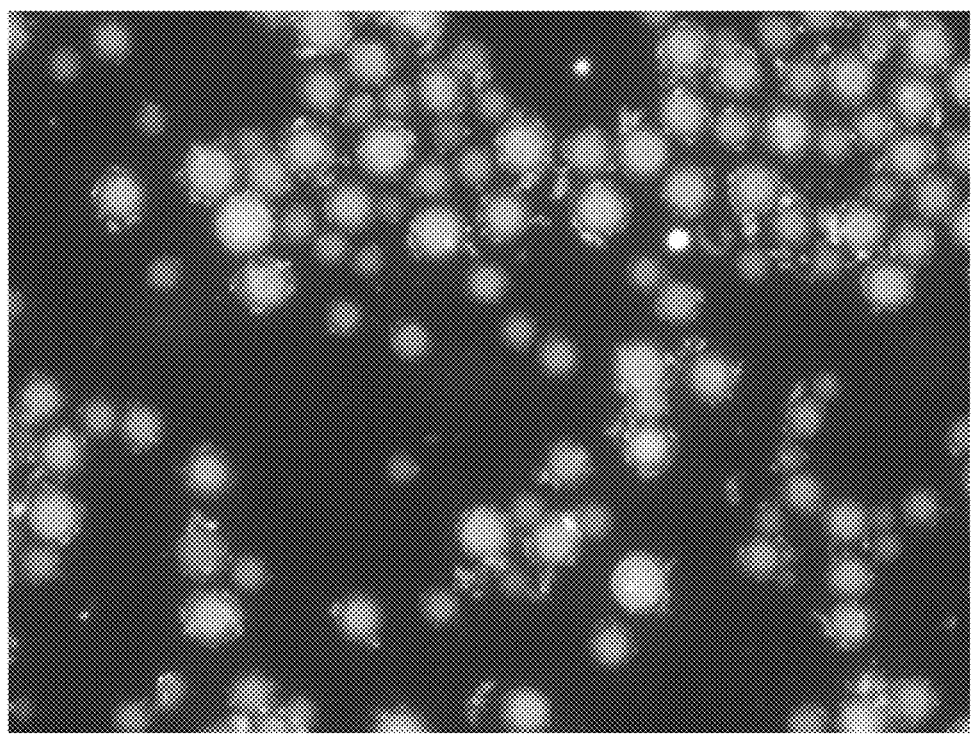
FIG. 4 is a microscope image of microparticles of Example 4 after the second procedure for coupling to a chelating agent and prior to sonication.
Figure 5:
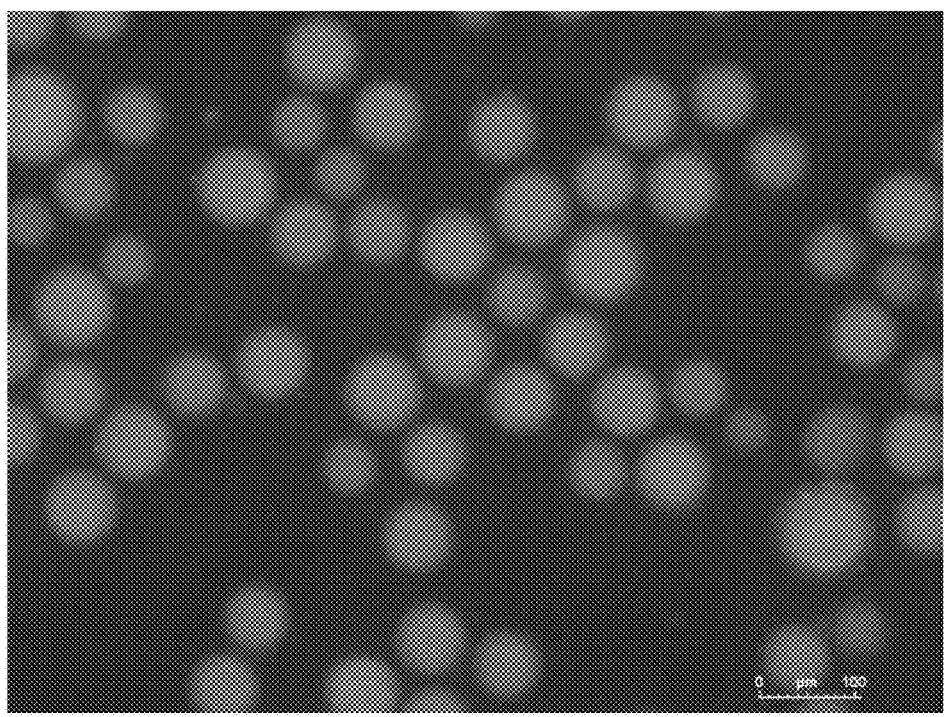
FIG. 5 is a microscope image of microparticles of Example 4 after the second procedure for coupling to a chelating agent and after sonication.

The microscopy results for the microspheres of the second procedure of Example 4 before sonication are shown in FIG. 4. The microscopy results for the microspheres of the second procedure of Example 4 after sonication are shown in FIG. 5. As shown in the images, the microspheres formed by coupling of the microspheres of Example 4 with MAG-3 are substantially spherical.

EXAMPLE 5

An Additional Example of Approach 1

An additional example of Approach 1 is the following:

A water/oil emulsion-suspension-polymerization method was used to prepare microspheres using sodium acrylate monomer. In this method, 6.75 gm of N,N-methylene-bis-acrylamide and 27 gm of sodium acrylate (97%) were added to 250 mL of an acetate buffer (prepared with 58 gm NaCl, 27.2 gm sodium acetate, 400 mL water and 300 mL glycerin, with the pH adjusted to 6.0 with acetic acid) at 40° C. The pH of the aqueous phase was adjusted with 50% aqueous acetic acid to maintain the pH at 6.0. The aqueous phase was filtered and an ammonium persulfate solution (0.34 gm of ammonium persulfate in 5 mL of water) was added. An emulsion was formed by dispersing the water phase into the oil phase at 60° C. with a mechanical stirrer at 288 rpm. One mL of TEMED (N,N,N',N'-tetraethylmethylenediamine) was added to catalyze the reaction. The emulsion was stirred for 90 minutes. When the polymerization reaction was completed, a saline solution (2.7% aqueous NaCl) was added and the suspension was centrifuged at 3500 rpm for 5 minutes. Microspheres were separated from the supernatant and washed 4 times with saline solution. Microspheres were acidified at pH 1.5 with HCl 1N and washed twice with saline solution and 6 times with deionized water.

A sample of the microspheres were suspended in 0.9% aqueous NaCl for granulometry analysis (Ellix software). The results showed that the diameter of the microspheres ranged from between about 11.66 μm and about 68.24 μm, with a mean diameter of about 30.23 μm.

The morphology of the microspheres was evaluated before and after lyophilization, using an optical microscope linked to a computer for analysis of the images.

Figure 6:
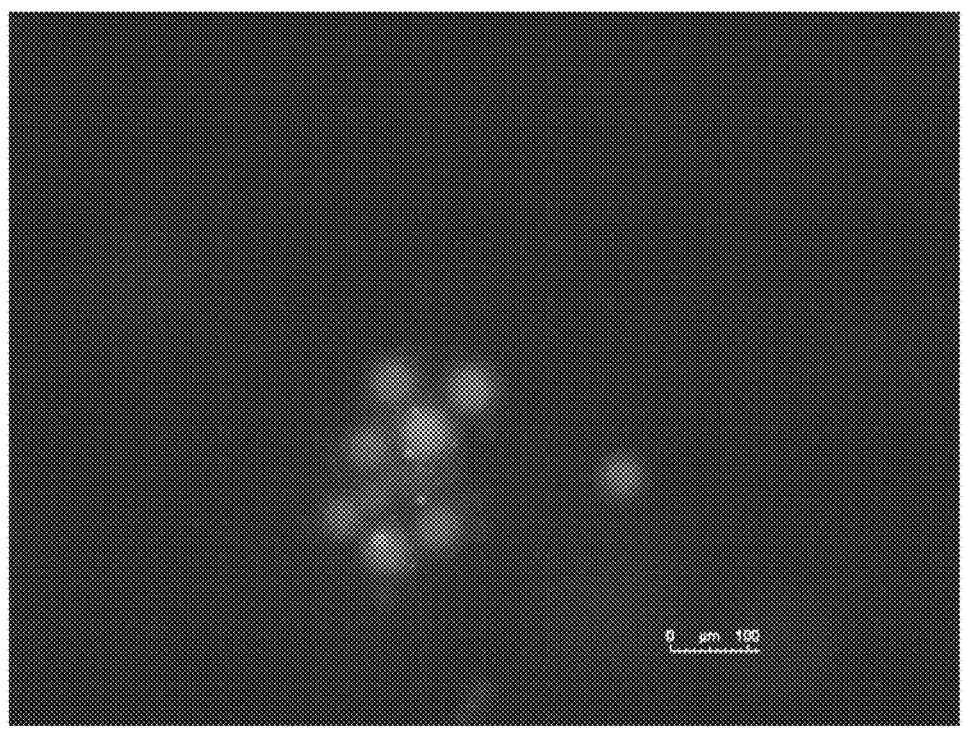
FIG. 6 is a microscope image of microparticles of Example 5 before lyophilization and prior to coupling to a chelating agent.
Figure 7:
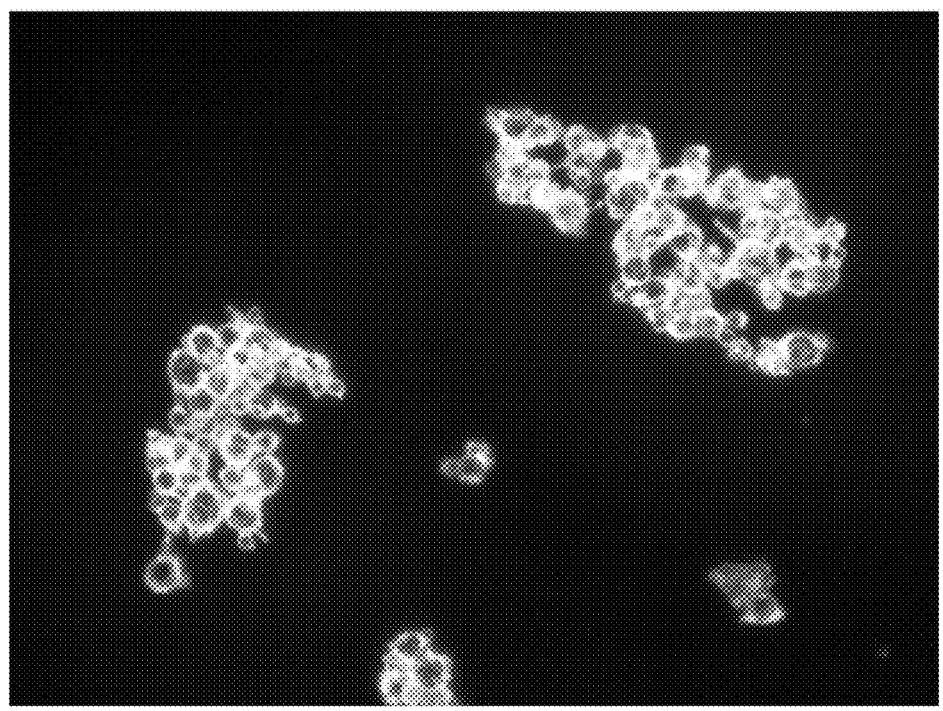
FIG. 7 is a microscope image of microparticles of Example 5 after lyophilization and prior to coupling to a chelating agent.

The microscopy results for the microspheres of Example 5 before lyophilization are shown in FIG. 6. The microscopy results for the microspheres of Example 5 after lyophilization are shown in FIG. 7. As shown in the images, the microspheres formed in Example 5 are substantially spherical.

Coupling of the Microparticles of Example 5 with MAG-3 Ligand

The following procedure was used for coupling the MAG-3 ligand to the microparticles of Example 5.

Dry microspheres (250 mg) were dispersed in 4.5 mL of DMF solvent. The DIEA (52.5 mg) and the HCl salt of Compound 12 (98 mg) were added to the slurry. The suspension was placed in an ice bath and HATU (81 mg) was added to the suspension at 0° C., whereupon the suspension turned fluorescent yellow. The suspension was kept at 0° C. for 1 hour and at room temperature for 21 hours. The microspheres were separated from the supernatant and washed 4 times with deionized water.

The same general procedure was used for coupling of the MAG-3 ligand to a sample of carboxylate-functionalized polystyrene microparticles (Polybeads® available from Polysciences, Inc. (Ellelhieim, Germany)) at a size of 20 μm. Dry microspheres (25 mg) were dispersed in 2.7 mL of DMF solvent. The DIEA (5.2 mg) and the HCl salt of Compound 12 (9.8 mg) were added to the slurry. The suspension was placed in an ice bath and HATU (8.1 mg) was added to the suspension at 0° C., whereupon the suspension turned fluorescent yellow. The suspension was kept at 0° C. for 1 hour and at room temperature for 19 hours. The microspheres were separated from the supernatant and washed 4 times with deionized water.

EXAMPLE 6

An Example of Approach 2

An example of Approach 2 is shown in the following scheme:

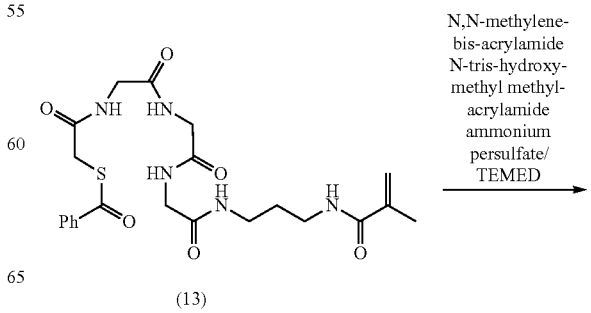

(13)

-continued

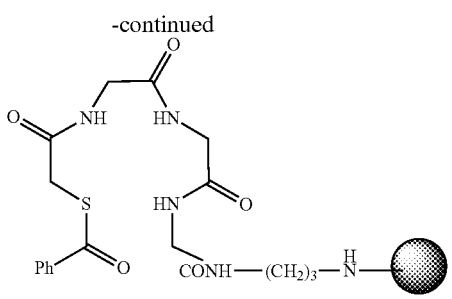

A water/oil emulsion-suspension polymerization method was used to prepare microspheres containing the MAG-3 chelating group. Compound 13 (1.08 gm) was dissolved in 50 mL of a pH 6 sodium acetate buffer. N,N-Methylene-bis-acrylamide (6.75 gm) and N-tris-hydroxy-methyl methylacrylamide (25.92 gm) were added to the solution of Compound 13, and the volume was adjusted to 200 mL with additional buffer. The solution was heated to 50° C. The aqueous phase was filtered and an aqueous solution of ammonium persulfate (0.34 gm in 5 mL of water) was added. The mixture was poured into 1 L of paraffin oil containing 3.5 gm of a surfactant (Arlacel). An emulsion was formed by dispersing the water phase into the oil phase at 60° C. with a mechanical stirrer at 288 rpm. One mL of TEMED (N,N,N',N'-tetraethylmethylenediamine) was added to catalyze the reaction. The emulsion was stirred for at least 90 minutes, at which time deionized water was added and the suspension centrifuged at 3500 rpm for 5 minutes. The microspheres were separated from the supernatant and washed four times with deionized water.

These microspheres contain approximately 3% of Compound 13 as determined by the amount of Compound 13 used in the monomer mixture subjected to polymerization.

EXAMPLE 7

An Additional Example of Approach 2

An additional example of Approach 2 is the following:

A water/oil emulsion-suspension polymerization method was used to prepare microspheres containing the MAG-3 chelating group. Compound 13 (2.15 gm) was dissolved in 50 mL of a pH 6 sodium acetate buffer. N,N-Methylene-bis-acrylamide (6.75 gm) and N-tris-hydroxy-methyl methylacrylamide (24.85 gm) were added to the solution of Compound 13, and the volume was adjusted to 200 mL with additional buffer. The solution was heated to 50° C. The aqueous phase was filtered and an aqueous solution of ammonium persulfate (0.34 gm in 5 mL of water) was added. The mixture was poured into 1 L of paraffin oil containing 3.5 gm of a surfactant (Arlacel). An emulsion was formed by dispersing the water phase into the oil phase at 60° C. with a mechanical stirrer at 288 rpm. One mL of TEMED (N,N,N',N'-tetraethylmethylenediamine) was added to catalyze the reaction. The emulsion was stirred for at least 90 minutes, at which time deionized water was added and the suspension centrifuged at 3500 rpm for 5 minutes. The microspheres were separated from the supernatant and washed four times with deionized water.

These microspheres contain approximately 6% of Compound 13 as determined by the amount of Compound 13 used in the monomer mixture subjected to polymerization.

Analysis of the Microspheres of Examples 6 and 7

A sample of each of the microspheres formed from Examples 6 and 7 were suspended in 0.9% aqueous NaCl for granulometry analysis (Ellix software). The results are shown in the following table:

| Microspheres | Diameter minimum (µm) | Diameter maximum (µm) | Mean diameter (µm) |
| --- | --- | --- | --- |
| 3% Compound 13 | 15.91 | 102.61 | 38.21 |
| 6% Compound 13 | 14.59 | 118.22 | 46.92 |

The morphology of the microspheres and their dispersability were evaluated using an optical microscope linked to a computer for analysis of the images.

Figure 8:
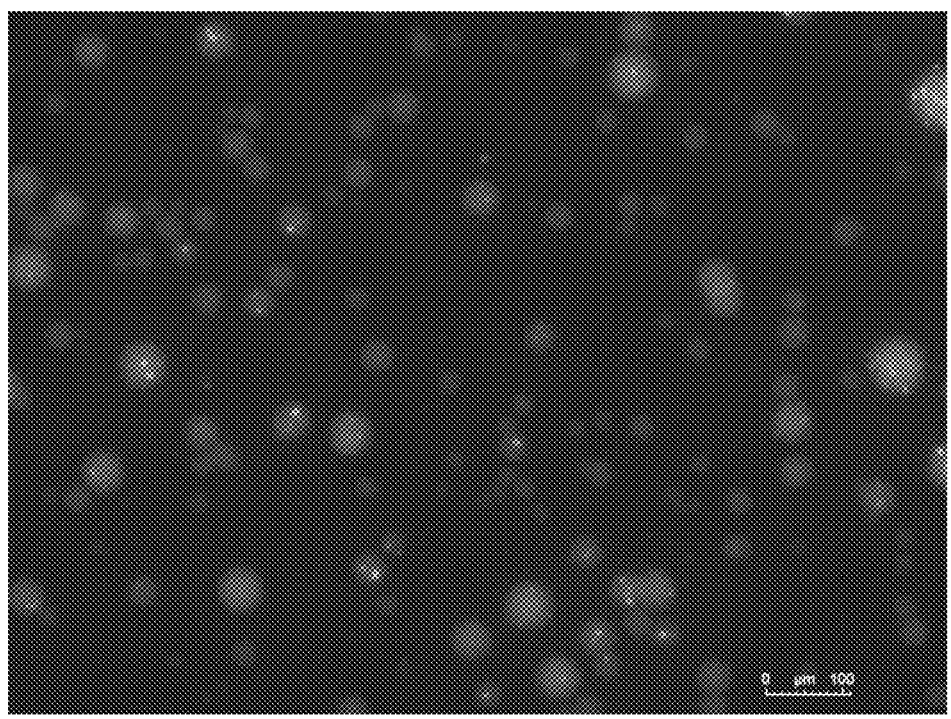
FIG. 8 is a microscope image of microparticles of Example 6 after coupling to a chelating agent.

The microscopy results for the microspheres of Example 6 are shown in FIG. 8. As shown in the images, the microspheres formed in Example 6 are substantially spherical.

Figure 9:
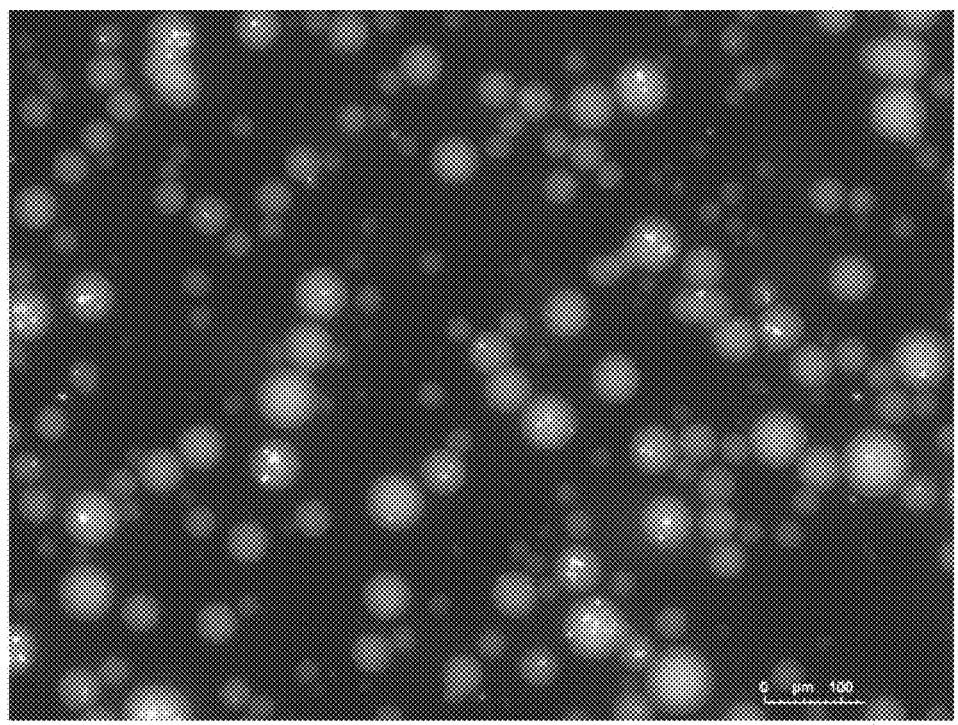
FIG. 9 is a microscope image of microparticles of Example 7 after coupling to a chelating agent.

The microscopy results for the microspheres of Example 7 are shown in FIG. 9. As shown in the images, the microspheres formed in Example 7 are substantially spherical.

Figure 10:
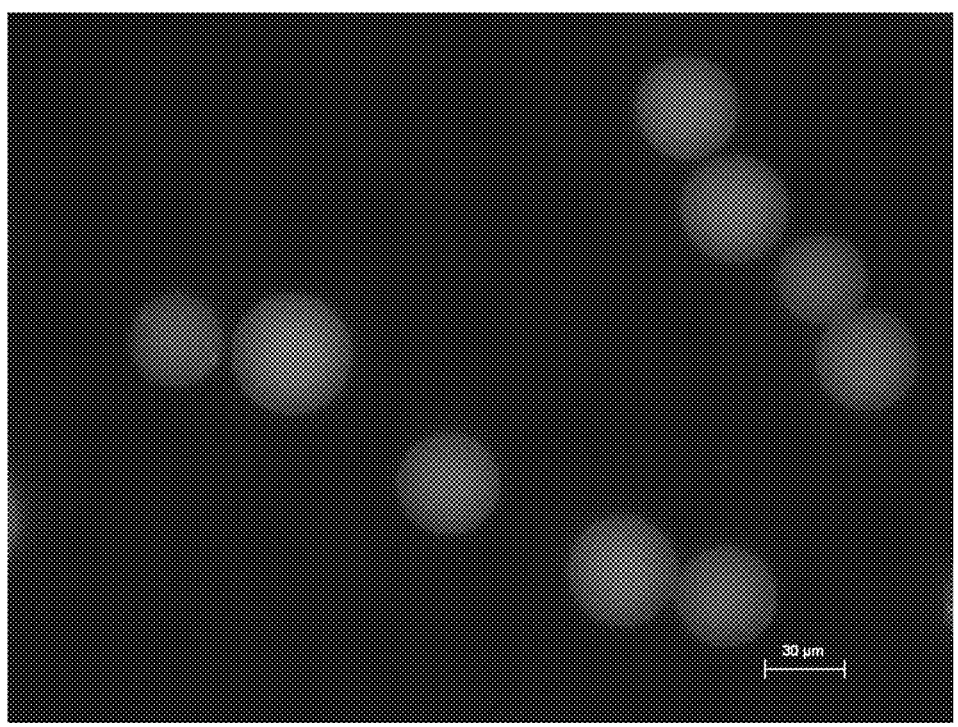
FIG. 10 is a microscope image of microparticles of Example 7 after coupling to a chelating agent and after sieving.
Figure 11:
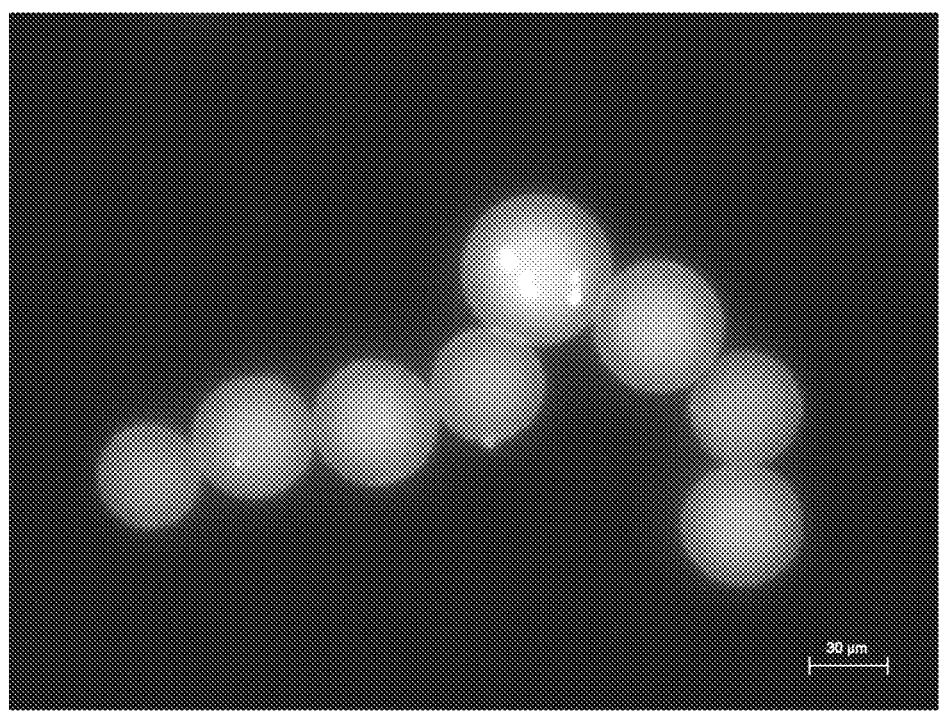
FIG. 11 is an additional microscope image of microparticles of Example 7 after coupling to a chelating agent and after sieving.

The microspheres may be sieved to get a desired size range. For example, the microspheres of Examples 6 and 7 were sieved after the microscopic images were taken, to a size range of between about 20 µm and about 40 µm. FIGS. 10 and 11 show microscopy results for samples of sieved microspheres of Example 7.

EXAMPLE 8

Another Example of Approach 2

An additional specific example of Approach 2 is the following:

In a beaker containing 100 mL of demineralized water, 58 g of sodium chloride and 27 g of sodium acetate are dissolved. One adds 400 mL of glycerol and then the pH is adjusted between 5.9 and 6.1. Then 90 g of N-tris-hydroxy-methyl methylacrylamide, 35 gm of Compound 13, and 10 g of N,N-methylene-bis-acrylamide are added. One heats at 60-70° C. and 100 mL of a hot 300 mg/ml gelatin solution is added. The total volume of the mixture is adjusted to 980 ml by addition of hot water and then 20 ml of a 70 mg/ml ammonium persulfate solution and 4 ml of N,N,N',N'-tetramethylethylenediamine are added.

This solution is poured into paraffin oil at 50-70° C. with stirring. After a few minutes, the polymerization reaction of acrylic monomers is manifested by an increase of temperature. The microspheres are then recovered by decanting, washed carefully, screened and sterilized in an autoclave in a buffered medium.

After recovery of the spheres, the gelatin may be reticulated by means of a 25% glutaraldehyde solution. The treatment is carried out with stirring at 4 C overnight. It is followed by a washing with demineralized water.

Chelation of Rhenium with the MAG-3 Ligand Coupled to a Microsphere

The MAG-3 chelating group may be used to chelate a radioisotope, such as [188]Rhenium, via the following synthetic route:

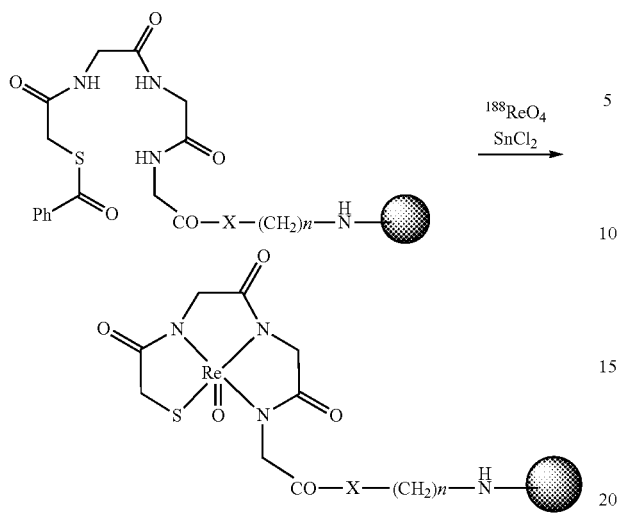

EXAMPLE 9

Chelation of Rhenium with MAG-3 Linked Microspheres

A sample of the microspheres from any of Examples 4, 5, 6, 7, or 8 is treated with a salt of radioactive perrhenic acid $[^{188}ReO_4]^-$, obtained from an on-site $^{188}W/^{188}Re$ generator, in a 0.5 M phosphate buffer at an appropriate pH, and $SnCl_2$ dihydrate in 0.05N HCl, and allowed to stand at 60° C. for 30 minutes. The sample is centrifuged at 1600×g for 10 minutes, the supernatant is removed, and the microspheres are suitable for use in the radio-embolization of a patient.

EXAMPLE 10

An Additional Example of Chelation of Rhenium with MAG-3 Linked Microspheres A sample of the microspheres from any of Examples 4, 5, 6, 7, or 8 may also be treated with one mL of a $^{188}Re$ sodium perrhenate eluate in 0.9% saline (NaCl in water), then mixed in a glass vial with 30 mg ascorbic acid, 40 mg potassium oxalate and 7.8 mg of $SnCl_2$. Approximately 5 mg of microspheres are then added to the solution. The reaction may occur at room temperature or at 90° C. The rate of the reaction increase when the solution is heated. After approximately one hr, the microspheres are centrifuged and the sediment may be washed with 0.1 N HCl and twice with water.

Those skilled in the art will recognize, or be able to ascertain using no more than routine experimentation, many equivalents to the specific embodiments of the invention described herein. Such equivalents are intended to be encompassed by the following claims.

The invention claimed is:

1. A method of preparing an embolic microsphere, comprising:
    fabricating a polymeric microsphere comprising a polymerized monomer and a chelating agent, wherein fabricating comprises:
        obtaining a monomer, wherein the monomer comprises at least one of an acrylate, acrylamide, acrylic, or monomer; and
        polymerizing the monomer with a chelating agent comprising a polymerizable group, wherein the chelating agent comprises a compound of Formula I:

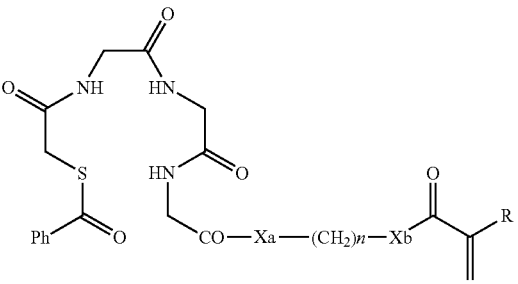

Formula I wherein n is between 1 and 18, inclusive;
Xa and Xb may independently be O, S or N; and
R may be alkyl or H,
wherein the polymerizable group of the chelating agent is polymerized with the monomer, wherein the chelating agent is configured to chelate a radioisotope, wherein the microsphere comprises between about 1% and about 20% by weight of chelating agent, wherein the microsphere comprises a diameter ranging from about 1 micrometer to about 2000 micrometers, and wherein the microsphere is suitable for embolization.

2. The method of claim 1, wherein at least one of Xa and Xb is O.

3. The method of claim 1, wherein the monomer comprises an acrylamide.

4. The method of claim 1, wherein the monomer is selected from at least one of the following: N-[tris(hydroxymethyl)methyl]-acrylamide or sodium acrylate.

5. The method of claim 1, wherein the monomer comprises N-[tris(hydroxymethyl)methyl]-acrylamide.

6. The method of claim 5, wherein the chelating agent is incorporated into a polymer of the polymeric microsphere.

7. The method of claim 1, wherein the method further comprises:
    associating the microsphere with a radioisotope.

8. The method of claim 7, wherein the radioisotope is both a β- and γ emitter.

9. The method of claim 7, wherein the radioisotope is selected from at least one of the following: $^{90}Y$, $^{32}P$, $^{99m}Tc$, $^{111}In$, $^{67}Ga$, $^{166}Dy$, $^{201}Th$, $^{131}I$, $^{140}La$, $^{153}Sm$, $^{165}Dy$, $^{166}Ho$, $^{169}Er$, $^{175}Yb$, $^{177}Lu$, $^{186}Re$, or $^{188}Re$.

10. The method of claim 7, wherein the radioisotope is not leached from the microsphere to an extent greater than about 3% of its original level by weight over a period of three months.

11. A method of preparing an embolic microsphere, comprising:
    fabricating a polymeric microsphere comprising a polymerized monomer and a chelating agent, wherein fabricating comprises:
        obtaining a monomer, wherein the monomer comprises an acrylamide, and
        polymerizing the monomer with a chelating agent comprising a polymerizable group, wherein the chelating agent comprises a compound of Formula I:

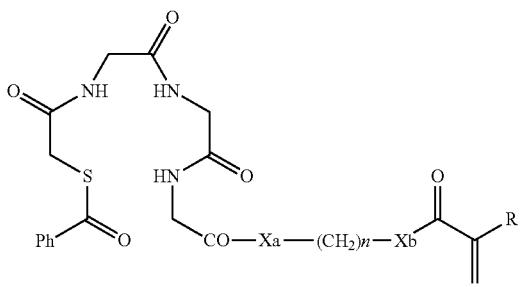

Formula I wherein n is between 1 and 18, inclusive;

Xa and Xb may independently be O, S or N; and

R may be alkyl or H, wherein the polymerizable group of the chelating agent is polymerized with the monomer and incorporated into a polymer of the polymeric microsphere, wherein the chelating agent is configured to chelate a radioisotope, wherein the microsphere comprises between about 1% and about 20% by weight of chelating agent, and wherein the microsphere comprises a diameter ranging from about 1 micrometer to about 2000 micrometers.

12. The method of claim 11, wherein at least one of Xa and Xb is O.

13. The method of claim 11, wherein the method further comprises:

associating the microsphere with a radioisotope.

14. The method of claim 11, wherein the radioisotope is selected from at least one of the following: $^{90}$Y, $^{32}$P, $^{99m}$Tc, $^{111}$In, $^{67}$Ga, $^{166}$Dy, $^{201}$Th, $^{131}$I, $^{140}$La, $^{153}$Sm, $^{165}$Dy, $^{166}$Ho, $^{169}$Er, $^{175}$Yb, $^{177}$Lu, $^{186}$Re or $^{188}$Re.

15. The method of claim 11, wherein the microsphere is non-biodegradable.

16. The method of claim 1, wherein the microsphere is non-biodegradable.

* * * * *

UNITED STATES PATENT AND TRADEMARK OFFICE
CERTIFICATE OF CORRECTION

PATENT NO. : 10,434,200 B2
APPLICATION NO. : 15/615586
DATED : June 6, 2017
INVENTOR(S) : Reb et al.

Page 1 of 1

It is certified that error appears in the above-identified patent and that said Letters Patent is hereby corrected as shown below:

In the Claims

Column 37, Line 66-67 reads, ". . . acrylamide, acrylic, or monomer . . ." which should read, ". . . acrylamide or acrylic monomer. . ."

Signed and Sealed this
Tenth Day of December, 2019

Andrei Iancu
*Director of the United States Patent and Trademark Office*